(12) United States Patent
Mahbub et al.

(10) Patent No.: US 12,160,185 B2
(45) Date of Patent: Dec. 3, 2024

(54) HIGH SURFACE AREA REVERSE ELECTROWETTING FOR A SELF POWERED WIRELESS WEARABLE MOTION SENSOR

(71) Applicant: UNIVERSITY OF NORTH TEXAS, Dallas, TX (US)

(72) Inventors: Ifana Mahbub, Dallas, TX (US); Russell Reid, Dallas, TX (US); Pashupati R. Adhikari, Dallas, TX (US); Nishat T. Tasneem, Dallas, TX (US); Dipon K. Biswas, Dallas, TX (US)

(73) Assignee: UNIVERSITY OF NORTH TEXAS, Dallas, TX (US)

( * ) Notice: Subject to any disclaimer, the term of this patent is extended or adjusted under 35 U.S.C. 154(b) by 365 days.

(21) Appl. No.: 17/703,870

(22) Filed: Mar. 24, 2022

(65) Prior Publication Data

US 2022/0311358 A1 Sep. 29, 2022

Related U.S. Application Data

(60) Provisional application No. 63/165,694, filed on Mar. 24, 2021.

(51) Int. Cl.
| | |
|---|---|
| *H03M 1/46* | (2006.01) |
| *A61B 5/00* | (2006.01) |
| *A61B 5/11* | (2006.01) |
| *G01P 13/00* | (2006.01) |
| *H02N 1/08* | (2006.01) |
| *H03F 3/45* | (2006.01) |
| *H02M 7/06* | (2006.01) |

(52) U.S. Cl.
CPC ............. *H02N 1/08* (2013.01); *A61B 5/0004* (2013.01); *A61B 5/11* (2013.01); *G01P 13/00* (2013.01); *H03F 3/45264* (2013.01); *H03M 1/46* (2013.01); *A61B 2560/0214* (2013.01); *H02M 7/06* (2013.01); *H03F 2203/45156* (2013.01); *H03F 2203/45526* (2013.01)

(58) Field of Classification Search
CPC .. H03M 1/46; H03M 1/12; G08B 1/08; G08B 1/00; H04B 1/00; H04B 1/04; H04B 1/0007; H04B 17/00; H04B 17/10; A63B 24/00; A63B 24/0003; A63B 24/0062
USPC ............................................. 73/488; 324/340
See application file for complete search history.

(56) References Cited

U.S. PATENT DOCUMENTS 11,374,587 B1 * 6/2022 Huynh ..................... H04B 5/48

* cited by examiner

*Primary Examiner* — Hai L Nguyen
(74) *Attorney, Agent, or Firm* — Conley Rose, P.C.

(57) ABSTRACT

A motion sensor device comprises: a reverse electrowetting-on-dielectric (REWOD) generator configured to generate alternating current (AC) based on motion; a motion sensor configured to measure motion data; and a wireless motion sensor read-out circuit coupled to the REWOD generator and the motion sensor, the wireless motion sensor read-out circuit configured to transmit the motion data and operate on the AC from the REWOD generator.

17 Claims, 4 Drawing Sheets

HIGH SURFACE AREA REVERSE ELECTROWETTING FOR A SELF POWERED WIRELESS WEARABLE MOTION SENSOR

CROSS-REFERENCES TO RELATED APPLICATIONS

This application claims the benefit of U.S. Provisional Application No. 63/165,694, filed on Mar. 24, 2021, and entitled "HIGH SURFACE AREA REVERSE ELECTROWETTING FOR SELF POWERED WIRELESS WEARABLE MOTION SENSOR," which is incorporated herein by reference in its entirety for all purposes.

STATEMENT REGARDING FEDERALLY SPONSORED RESEARCH OR DEVELOPMENT

This invention was made with government support under Grant No. ECCS 1933502 awarded by the National Science Foundation. The government has certain rights in the invention.

BACKGROUND

Generally, wireless wearable sensors can monitor a person's health conditions. Monitoring human health in real-time using wearable and implantable electronics (WIE) has become one of the most promising and rapidly growing technologies in the healthcare industry. In general, these electronics are powered by batteries that require periodic replacement and maintenance over their lifetime. To prolong the operation of these electronics, they should have zero post-installation maintenance. To overcome this shortcoming, such sensors are desired to be combined with a self-powered system to power such sensors.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
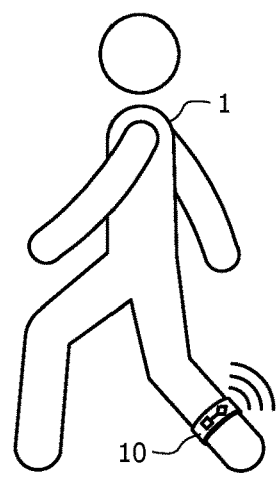
FIG. 1 is a schematic depiction of a person wearing a motion sensor device according to an embodiment.

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques below, including the exemplary designs and implementations illustrated and described herein, but may be modified within the scope of the appended claims along with their full scope of equivalents.

Generally, embodiments relate to a wearable motion sensor device that can operate without an independent power source. The motion sensor device includes a motion sensor that measures motion data. The motion sensor device also includes a reverse-electrowetting on dielectric (REWOD) generator that generates alternating current (AC) when worn based on user motion. The motion sensor device also includes a motion sensor transmitter circuit. The motion sensor transmitter circuit includes an amplifier to amplify the motion data, an analog to digital converter (ADC) to convert the motion data into a digital format, and a transmitter to transmit the motion data. The motion sensor transmitter circuit also includes a rectifier and a voltage regulator to convert the AC voltage/current from the REWOD generator into a DC power to power-up the amplifier, the ADC, and the transmitter. In this way, the motion sensor can operate and wirelessly transmit motion data based solely on the power supplied by the wearer via motion.

With the development in the healthcare industry, extensive research has been carried out in the areas of sensors to remotely monitor healthcare activities. In an approach to eliminate the need of periodic battery replacement and maintenance, wearable and self-powered sensors have attracted a great deal of attention. Energy harvesting can include the process of transducing ambient kinetic or mechanical energy into electrical energy. The energy sources can be of various forms such as heat, light, pressure, vibration, electrostatic, and sound that may be harnessed for the sustainable driving of the wearable medical devices. Recently, an electrostatic energy harvesting technique called triboelectricity has been introduced that can operate at various frequencies with high power output. However, the triboelectric generators have a short life-span due to the continuous friction between the electrodes, thus decaying the energy efficiency. Other designs include flexible, fiber-based energy harvesting generators (FBG) that convert the bio-mechanical vibration energy to electrical energy, involving conducting fibers integrated into clothing. The current generation in FBG is too low (typically 0.1 $\mu W/cm^2$) to reliably power medical devices. Other designs include transducers utilizing nanotechnology to maximize power density using body heat through flexible materials while simultaneously minimizing the power consumption by incorporating CMOS circuitry working in the sub-threshold region and ultra-low-power radios. To miniaturize electronic devices integrated with energy harvesters to power wearable sensors, energy density is a key factor to power these sensors. Owing to the limitations of various energy harvesters that could potentially power wearable sensors in health monitoring, energy harvesting based on mechanical motion of liquid electrolyte between the electrodes to generate alternating current has been identified and is known as reverse electrowetting on dielectric (REWOD) energy harvesting.

REWOD can generate very high-power densities at low driving frequencies compared to the conventional kinetic energy harvesters. Because many energy harvesters operate at a fairly high resonant frequency, they cannot be used in motion activity detection sensors operated at low frequency (<10 Hz). The harnessed power from a REWOD generator due to various low-frequency movements such as walking and running can provide power to an internal circuit such as a CMOS Integrated Circuit. The energy harvesting circuit typically includes a rectifier for the AC-DC power conversion and a DC-DC converter for the supply voltage regulation. As the sensor front-end circuit, an amplifier is designed to amplify the generated electrical signal by the transducer, followed by an analog-to-digital converter to digitize the signal and a transmitter circuitry to transmit the sensed signal wirelessly to a remote receiver.

A rectifier with the capability to rectify a low input power is one of the most desirable units in energy harvesting circuit for low power wireless sensors. However, the conventional diodes require about 0.7 V of input forward-bias voltage that may limit the operation of the rectifier. Another approach uses a Schottky diode based rectifier due to the low forward-bias voltage requirements of the Schottky diode. In the sensor front-end circuitry, several architectures of the charge amplifier may be used. In order to improve the transconductance, DC gain, and input-referred noise performance of the conventional FC-OTA, current reusing technique can be introduced. As the charge amplifier may be required to have a high gain (>40 dB) depending on the transducer's charge generation with very low power consumption (<2 µW) for biomedical applications, the designed OTA can utilize the recycling folded-cascode (RFC) technique. With the enhancement in transconductance, the amplifier may be prone to instability as the phase-margin could be reduced. In an embodiment, the architecture of the fully-differential charge amplifier also can enhance the phase-margin as well as reduce the input-referred noise, thus making the system stable. In order to digitize the amplified signal, a successive approximation register-ADC (SAR-ADC) has been the most widely used architecture for its low-power consumption at a low sampling rate, making it suitable for low-frequency biomedical sensor applications. Some embodiments herein can provide a SAR-ADC based on the charge redistribution network with a target of maintaining low-power operation. At the transmitting end, impulse radio ultra-wideband (IR-UWB) transmitter can be suitable for low-power application. By using duty-cycled IR-UWB transmitter, the system can maintain a strict power budget. Generally, the transmitter also needs to comply with the spectrum regulation imposed by the Federal Communication Commission (FCC) for UWB communication that requires the peak power spectral density to be lower than −41.3 dBm/MHz.

In some embodiments, further disclosed herein are: (a) modeling and fabrication of a REWOD based energy harvester that can harvest current at a specified current range (e.g., in an embodiment can harvest 20-90 ηApp of current at a frequency range of 1-10 Hz), (b) an on-chip charge amplifier (e.g., that can in some embodiments have 53.7 dB gain), (c) a multi-stage Schottky diode based rectifier (e.g., a seven-stage Schottky diode based rectifier that achieves a maximum power conversion efficiency (PCE) of at least about 55%, at least about 60%, or at least about 62%), (d) an eight-bit SAR-ADC, and (e) an IR-UWB transmitter with reconfigurable frequency and bandwidth features working in the 3.1 to 5 GHz frequency band.

In some embodiments, there are various techniques to voltage rectification and DC-DC boosting of an AC signal of low magnitude without external bias source. One of the advantages of these techniques is that an AC signal originating from various energy harvesters can be converted and boosted to constant DC source of higher magnitude that can potentially power wearable sensors for real time human health monitoring. Among various energy harvesting technologies such as piezoelectric, electromagnetic, vibration-based, and reverse electrowetting on-dielectric energy harvesting (REWOD), REWOD can harvest energy from low frequency motion such as many human notion (walking, running, jogging etc.).

Voltage rectification and DC-DC boosting of low magnitude AC voltage from REWOD can be used to reliably self-power the wearable sensors in REWOD energy harvesting. A mechanical input during the motion causes the electrolyte placed in between two dissimilar electrodes to squeeze back and forth thereby periodically changing the effective interfacial area and hence generating alternating current. As an example, an unconditioned REWOD output of 95-240 mV AC can be generated using a 50 µL droplet of 0.5M NaCl electrolyte and 2.5 mm of electrode displacement from an oscillation frequency range of 1-3 Hz. Commercial off-the-shelf components (COTS) that may involve the integrated circuit design of the CMOS process, making it a highly miniaturized system. Electric potential difference of 135-240 mV and a forward current of 1 mA convert the generated AC signal to DC voltage. The electric potential difference of 3 V DC is measured at the boost converter output, thereby the system can function as a self-powered motion sensor. For another approach, consider a full-wave rectifier or bridge rectifier consists of p-n junction diodes, which may not be suitable for very low input voltage, as such a rectifier may require 0.7 V forward bias voltage to conduct. Similarly, for DC-DC converter the Dickson charge pump is one possibility that may be used as a DC-DC boost converter, but the input voltage can be high because of the forward voltage requirement of traditional diodes. Hence, cross-coupled switched-capacitor circuits may be better for low input voltage boosting. For a rectifier, the highly efficient voltage-boosting rectifier can have a wider frequency operation range of 10 kHz-100 MHz. One particular rectifier can achieve a power conversion efficiency (PCE) of up to about 51% with 100 mV at 7.25 MHz input signal, which may be highly applicable for the inductive-coupling based wireless power transfer applications for implantable sensors.

One system can achieve very high efficiency of up to about 95.5% at 0.2 V at 100 Hz. The technique uses DTMOS, where the body terminal can be connected to the gate in a diode-connection form. This factor helps in rectifying the input voltage with wider dynamic control over the threshold voltage. Not only the frequency of the input signal plays a role, but also the startup voltage plays a major role in the efficient operation of the circuit. Another system can provide a charge pump circuit designed in a standard 0.18 µm CMOS process. The system can consist of six stages for each stage with a 24 pF pumping capacitor the minimum start-up required that is 350 mV output voltage rise from 0 to 2.04 V within 0.1 milliseconds, generally being unsuited for input voltage amplitude of 100 mV. A similar shortcoming can be observed in a further system where the PCE dropped by more than 50% when the input voltage is reduced from 500 mV to 220 mV. But at 500 mV, the VCE and PCE are 90% and also for this system, the minimum operating voltage is 380 mV. Similarly, for the DC-DC voltage booster, the charge pump circuit may be used to regulate the output DC voltage. Apart from that, buck-boost converters may also be a better technique for DCDC conversion. An inductorless DC-DC converter may be used for micro-power harvesting, as it may provide output regulation at 1.4 V with up to about 58% power conversion efficiency but, the minimum input voltage for this design is typically 270 mV. When connected to a sinusoidal source of 3.3 V peak amplitude, the overall power efficiency can be improved by 11% compared to other converters given by a gate cross-coupled-based structure due to its efficiency and input voltage and is unsuitable for low voltage design.

In some embodiments, remote health monitoring in real-time using wearable and implantable electronics (WIE) has become one of the most promising and rapidly growing technologies in the healthcare industry. Often powered by battery, these remote health monitoring electronics can be much more reliable and cost effective if the primary source of the power, the batteries, are replaced by an energy harvesting system. The system can harvest energy from various human motion activities, such as walking, running, jogging, and several other physical activities. Batteries not only occupy most of the space in the electronics, but also add significant weight and cause safety issues due to possible electrolyte leakage that is flammable in nature. Collectively, these issues also go against the portability of the wearables. Although significant progress has been made in increasing the capacity of the batteries and reducing the power consumption of the devices, these systems require rigid batteries with frequent replacement or charging process, which greatly limits their application and brings inconvenience to the user. Therefore, there is an urgent need to develop an energy harvesting system that can consistently and sufficiently generate power without any external bias source and operate solely based on the energy harvested from human motion activities. As a result, this will help improve the longevity and reliability of these electronics for human health monitoring in real-time.

In some embodiments, various well-established energy harvesting technologies have emerged over the years such as vibrational, thermoelectric, piezoelectric, and electromagnetic energy harvesting. While these technologies have received significant attention in research and are reliably used for specific applications, most, if not all, fail to harvest energy at lower frequency range (less than 5 Hz) with high power density. In addition, these energy harvesting technologies require resonance of solid structures to operate, which is typically over 30 Hz, making them quite unsuitable for harvesting energy from human motion-related activities. Based on the limitations of the existing energy harvesting technologies, energy harvesting based on reverse electrowetting-on-dielectric (REWOD) has been developed within the last decade. REWOD has been shown to operate efficiently at the typical frequency range of human motion (1-5 Hz). REWOD is opposite to electrowetting-on-dielectric (EWOD) in which an electric field applied to an electrolyte modifies the effective surface tension and produces electrolyte movement. In REWOD, applied mechanical modulation changes electrolyte displacement and thereby changes the electrode-electrolyte interfacial area, resulting in a periodic variation in capacitance. Due to the variation in capacitance, charges are drawn towards or discharged from the interface, and a voltage difference across the electrodes is realized. This mechanism is equivalent to a variable capacitor such that the energy harvested using REWOD is directly proportional to the interfacial capacitance. Prior research in REWOD has solely relied on planar electrodes, which by its geometry has a fixed interfacial area, limiting capacitance and hence power density output. In order to enhance the power density from REWOD energy harvesting, a mechanism is provided to increase the surface area of the electrodes by perforating silicon wafers with numerous micro-sized pores. These perforations can create a much higher surface area per planar area resulting in a much higher power density.

In one example, a high surface area REWOD configuration can have a porous electrode coated with dielectric materials (e.g., a $SiO_2$ and a fluoropolymer solution is sold under the trade designation CYTOP® by Asahi Glass Company, Limited Corporation of Tokyo, Japan, hereinafter "CYTOP®"). A conductive electrolyte can be inserted and retracted in and out of the pores under the application of a time varying pulsating pressure, P(t), thereby periodically modulating electrical capacitance and hence generating an AC voltage across the electrodes. The formation of electrical capacitance is due to the capacitance from the electrical double layer (EDL) at the solid-liquid interface and across the dielectric insulator. EDL capacitance is typically neglected because when combined in series with the dielectric layer capacitance, and the EDL capacitance is negligible. The effective capacitance can be modeled as given in Equation 1.

$$C = (\varepsilon_0 \varepsilon_r A)/d \qquad \text{Eq. (1)}$$

where $\varepsilon_0 = 8.85 \times 10^{-12}$ F/m is the vacuum permittivity, $\varepsilon_r$ is the relative permittivity of the dielectric material, A is the electrode-electrolyte interfacial area, and d is the thickness of the dielectric layer. Among all the parameters influencing the capacitance, electrode-electrolyte interfacial area plays a role in maximizing the capacitance and hence the output voltage.

In some embodiments, high surface area electrodes can possess much higher surface area as compared to its planar area and may be used as a REWOD energy harvester integrated to power WIEs, which have become significantly miniaturized over the years. With respect to powering miniaturized WIEs, power density, which is the power generated per unit area ($W/cm^2$), is one of the most important parameters to consider in REWOD energy harvesting. With respect to powering miniaturized WIEs, power density, which is the power generated per unit area ($W/cm^2$), is one of the most important parameters to consider in REWOD energy harvesting. While high surface area electrodes significantly enhance power output compared to planar electrodes, the absence of bias voltage can make the WIEs fully self-powered. In such a scenario, the voltage generated from the REWOD as an input can be rectified to convert the AC signal to a DC voltage and then boosted and regulated to supply a constant DC power by using a DC-DC converter. All of these components can be integrated within the WIEs and hence power the device without requiring an external voltage source and also contributing to miniaturization of the device. Generally, very few works address where the energy harvester is integrated with a rectifying circuit and is able to self-power analog circuits. A challenge of designing a rectification circuit can be operating the system at a very low frequency range. A commercially available power management unit has been used for low frequency energy scavenging. However, the system works at 7.8 Hz frequency. As the REWOD energy harvester works in the frequency range of 1-5 Hz, a rectification circuit that operates in the same frequency range can be designed to make the sensor self-powered. A rectifier circuit followed by voltage regulator circuit can be used to convert the harvested AC voltage to a constant DC voltage to power up the other analog circuitry such as amplifier, transmitter, and analog-to-digital converter (ADC).

In some embodiments, the REWOD can transduce the mechanical modulation between the two electrodes into an electric current, and possibly be suited for motion sensing applications. Several movement and activity tracking sensors may be used, such as accelerometers and pedometers. Even though these devices measure human physical activities, the devices can exhibit the shortfalls of storing long-term data and requiring a battery. In some embodiments, a self-powered REWOD motion sensor, which would wirelessly send the movement data to a remote receiver. The REWOD harvester can function as a motion tracking sensor, where the charge amplifier may produce an output voltage proportional to the generated charge from the motion activities. Typically, the generated AC charge lacks the capability of distinguishing motion at various frequencies and displacements due to low resolution. Thus, transducing and amplifying the low amount of charge achieves improved signal-to-noise ratio (SNR) as well as high dynamic range for the motion sensor. Having the charge amplifier ensures an overall better resolution for the self-powered motion sensor. An ADC may also be utilized to digitize the amplified signal and finally a transceiver (TX) can transmit the data wirelessly to a remote receiver.

REWOD is opposite to electrowetting-on-dielectric (EWOD) in which an electric field applied to an electrolyte modifies the effective surface tension and produces electrolyte movement. In REWOD, applied mechanical modulation changes electrolyte displacement and thereby changes the electrode-electrolyte interfacial area, generating alternating current.

An example of the REWOD configuration is the top electrode that may be coated with a metal layer acting as a current collector. The bottom electrode is first coated with a metal layer for conduction and then with a dielectric layer (e.g. $Al_2O_3$) with an additional layer of fluoropolymer (e.g., CYTOP® fluoropolymer) for surface hydrophobicity. An electrolyte is sandwiched between the electrodes which upon oscillation generates AC current due to a modulating electrical capacitance and thus an AC voltage across the electrodes. The formation of electrical capacitance is due to the capacitance from both the electrical double layer (EDL) at the solid-liquid interface and the dielectric insulator. The total capacitance can be modeled as: $C=\varepsilon_0\varepsilon_r A/d$ where $\varepsilon_0=8.85\times10^{-12}$ F/m is the vacuum permittivity, $\varepsilon_r$ is the relative permittivity of the dielectric material, A is the electrode-electrolyte interfacial area, and d is the thickness of the dielectric layer. Two possible ways the capacitance can be increased are by decreasing the dielectric thickness or by using dielectric materials with high $\varepsilon_r$. However, many high $\varepsilon_r$ materials have high thermal instability and resistivity. Dielectric materials such as $Al_2O_3$ are considered ideal for REWOD applications.

In some embodiments, one of the performance parameters of REWOD energy harvester is the power density, which is the power generated per unit area ($W/cm^2$). Power density is one of the parameters to consider in energy harvester design because wearable sensors have become significantly miniaturized over the years. There are two pathways to higher power density REWOD energy harvester output. One is the application of bias voltage in which an externally applied voltage induces high current and therefore results in high power density. However, the concept of "self-powered" is significantly compromised in that scenario because the application of an external voltage source no longer makes the device self-powered. On the other hand, much lower power density is achieved without applying any external bias voltage, but the power would not be sufficient to power wearable sensors. Therefore, the small input voltage from the REWOD can be rectified to convert the AC signal to a DC voltage and then boosted and regulated to supply a constant DC power by using a DC-DC converter. All of these components can be integrated within the same device and hence power the device without requiring an external voltage source. The input AC voltage from the REWOD may be fed into the rectifier and voltage regulator to rectify and regulate the DC power supply to the motion sensor. Eventually implementing the REWOD electrodes on a flexible and biocompatible material can allow the motion tracking device to be worn on the ankle, thus harvesting energy from regular physical activities. The figure also depicts the REWOD harvester functioning as a motion tracking sensor, where the charge amplifier amplifies the generated charge from the motion activity. Typically, the generated AC voltage amplitude from the REWOD lies in the mV range, lacking the capability of distinguishing motion at various frequencies and displacements due to low resolution. Amplifying the low amount of charge can achieve improved signal-to-noise ratio (SNR) as well as high dynamic range for the motion sensor. Having the charge amplifier thus ensures an overall better resolution for the self-powered motion sensor. An analog-to-digital converter (ADC) digitizes the amplified signal and finally a transmitter (TX) transmits the data wirelessly to a remote receiver, which is the eventual goal of this research.

In some embodiments, different architectures and design methods may be used to rectify a low input signal to a higher output power. A self-calibrating energy harvester may generate a 1 V input signal at −26.3 dBm input power that corresponds to 141 mVP-P input voltage. Similarly, a diode connected transistor-based rectifier circuit may rectify a low input signal of 200 mV. However, the prior architectures may only work at MHz frequency range. As the AC signal harvested from the REWOD is fairly low in frequency and amplitude, an efficient low frequency signal (less than 10 Hz) rectifying circuitry is required to convert the AC signal to DC signal. The AC voltage from the REWOD generated during electrode modulation due to motion activity is fed into a charge amplifier to produce an output voltage proportional to the generated charge. Both the standard commercial-off-the-shelf (COTS) and application-specific integrated circuits (ASIC) approaches for sensor integrated electronics (IE) can be considered. For complicated sensor IEs, e.g., pressure and tactile sensors, the ASIC approach is generally preferred. Previously reported charge amplifiers used in the transducers may not be suitable for low-frequency tracking sensors. For a low-frequency motion detection, a feedback control technique is implemented with the charge amplifier. Feedback path provides good linearity characteristics for low-bandwidth applications. In some embodiments, the standard COTS-based system is implemented in the motion detection circuitry, which is powered by the REWOD and the associated energy harvesting circuit. The motion sensor may also include the ADC and the TX to wirelessly transmit the motion sensor data to a remote end. The charge amplifier and the energy harvesting circuit design along with the transducer may be used for the self-powered wearable motion sensor application.

Self-powered sensors capable of zero-maintenance monitoring and data collection over days to weeks may not be available for many applications that do not have regular access to solar energy or wireless power transmission. In an example, this disclosure focuses on the hitherto unexploited surface area advantage of a liquid-based energy harvesting concept called reverse electrowetting to harvest energy from low-frequency movement and to develop a self-powered motion sensor to detect various movements such as walking and running. High surface area reverse electrowetting depends on reversible electrolyte movement within a porous electrode with applied pressure or an electric field. Example limiting parameters include electrode pore size, electrolyte conductivity, dielectric type or thickness, surface finish, and the pressure and voltage magnitude or frequency. These parameters may be modeled, improved, and experimentally validated to maximize available energy or power for a centimeter (cm) sized transducer. Reverse electrowetting may be capable of producing 1 milliwatt (mW)/cm$^2$ at <10 hertz (Hz) oscillation frequency through the use of high surface area materials and parameter optimization. These design parameters may be used in the selection and integration of highly porous electrode materials (e.g., sintered metal and buckypaper, in other words a thin sheet made from an aggregate of carbon nanotubes) with electrolyte, electret, and housing components for increased low-frequency energy harvesting in an about 5 cm$^3$ package. A miniaturized integrated circuit (IC) chip may make the energy harvester highly suitable for other industrial and biomedical applications. The system may include an integrated low-power wireless data transmission circuitry and miniaturized antenna on a flexible polydimethylsiloxane (PDMS) substrate for developing a self-powered, conformable motion sensor. This wearable sensor may be self-powered, low-cost, and may demonstrate high surface area reverse electrowetting's ability to harvest enough energy from low-frequency motion to entirely self-power a wearable motion sensor.

A high surface area reverse electrowetting can demonstrate reverse electrowetting in a flexible system and provide an efficient, improved, and efficient rectifier and direct current (DC)-DC converter topologies that can start-up with as low as 30 millivolt (mV) input voltages and an integrated self-powered motion sensor with wireless data transmission capability. This technology can support the development of self-powered devices capable of long-term motion sensing useful for monitoring post-operative elderly patients who are recovering from procedures such as joint replacement surgery. The self-powered motion sensor relies on the harvested kinetic motion as an external energy source and is capable of long-term operation. Such a wireless sensor has not previously been demonstrated for low-frequency kinetic energy harvesting.

Some embodiments may include a motion sensor transmitter circuit. The motion sensor transmitter circuit is configured to receive motion data from a motion sensor and wirelessly transmit the motion data. The motion sensor transmitter circuit is also configured to operate based on power from a reverse-electrowetting on dielectric (REWOD) generator. The REWOD generator generates AC proportional to the motion frequency and displacement. The motion sensor transmitter circuit is configured to convert the AC into DC and employ the DC to power the transmitter to transmit the motion data from the motion sensor. The motion sensor transmitter circuit allows for the creation of a wearable motion sensor that is powered by the motions of the user. The REWOD generator creates energy as the user moves the motion sensor device and the motion sensor device measures such movement. The energy from the REWOD generator powers the motion sensor transmitter circuit, which receives and transmits the motion data. As such, no independent power source may be required, and the motion sensor transmitter circuit can allow for the operation of the motion sensor for long periods of time with little or no outside intervention.

In an example, a motion sensor device is disclosed. The motion sensor device comprises a REWOD generator configured to generate AC based on motion. The motion sensor device also comprises a motion sensor configured to measure motion data. The motion sensor device also comprises a motion sensor transmitter circuit coupled to the REWOD generator and the motion sensor. The motion sensor transmitter circuit may be configured to transmit the motion data and operate on the AC from the REWOD generator. For example, the REWOD generator may generate an AC from movements of a conductive droplet squeezed between two electrode substrates. Accordingly, when a user moves, the conductive droplet also moves, which creates the AC used to power the rest of the device. In an example, the motion sensor transmitter circuit may comprise a rectifier configured to convert the AC into DC. This allows the motion sensor transmitter circuit components to operate on DC instead of AC. The motion sensor transmitter circuit may also comprise a voltage regulator, which is configured to maintain the DC at a substantially constant voltage. In this way, the motion sensor transmitter circuit can operate using consistent power when the user is in motion.

In a further aspect, the motion data is measured in analog by the motion sensor. Accordingly, the motion sensor read-out circuit may further comprise an amplifier configured to amplify the motion data. This amplifier configuration can support more accurate processing of the motion data. The wireless motion sensor read-out circuit may further comprise an ADC configured to convert the amplified motion data into digital format for transmission. The wireless motion sensor read-out circuit may further comprise a transmitter configured to transmit the motion data. In an example, the amplifier, the ADC, and the transmitter are powered by the AC generated by the REWOD generator. For example, the substantially constant DC voltage from the voltage regulator can power the amplifier, the ADC, the transmitter and/or any other components in the wireless motion sensor read-out circuit based on the user movement that causes power generation at the REWOD generator.

In an example implementation, the wireless motion sensor read-out circuit may comprise a power input and a motion sensor input. The wireless motion sensor read-out circuit may also comprise a rectifier comprising a rectifier input and a rectifier output. The rectifier input is coupled to the power input. The wireless motion sensor read-out circuit may also comprise a voltage regulator comprising a voltage regulator input and a voltage regulator output. The voltage regulator input is coupled to the rectifier output. The wireless motion sensor read-out circuit may also comprise an amplifier comprising an amplifier input, an amplifier power and ground ports, and an amplifier output. The amplifier input is coupled to the motion sensor input. The amplifier power port is coupled to the voltage regulator output. The wireless motion sensor read-out circuit may also comprise an ADC comprising an ADC input, an ADC power and ground ports, and an ADC output. The ADC input is coupled to the amplifier output. The ADC power port is coupled to the voltage regulator output. The wireless motion sensor read-out circuit may also comprise a transmitter comprising a transmitter input, a transmitter power and ground ports, and an antenna. The transmitter input is coupled to the ADC output and the transmitter power port is coupled to the voltage regulator output.

In some embodiments, a charge amplifier can be used for converting the generated charge to a proportional output voltage. The amplifier may consist of a resistive-capacitive feedback network. The input impedance of the charge amplifier with the feedback network is designed in such a way to match the equivalent impedance of the REWOD transducer. The feedback resistor $R_f$ can be chosen to provide the DC path for the overall input currents of the operational transconductance amplifier (OTA). In some aspects, the value of $R_f$ can be selected to be 1 GΩ to achieve the high-pass frequency of about 0.88 Hz. The input and the feedback capacitance values are chosen to be 470 pF and 180 pF, respectively, to achieve the gain of 8.33 dB (2.6 V/V), in the pass band. A general-purpose amplifier (model no: ADA4691-2) from Analog Devices Inc. of Wilmington, MA may be used as the charge amplifier. The proportional output voltage from the amplifier ($V_{out}$) may be digitized using the twelve-bit ADC of CC430F5137. This chip is a low-power microcontroller with the RF transceiver integrated with it. The ADC may use an internal reference voltage of Vcc/2, where Vcc is the supply voltage of the transceiver (3.3V). The sampling frequency of the ADC may be 0.45 MHz, which can be set internally without using any external oscillator. The digitized signal is sent to a remote receiver through a ceramic antenna at 868 MHz with a transmission power of 0 dBm.

One voltage multiplier may be a Schottky diode-based two-stage Cockroft-Walton architecture. A SC7630-079LF Schottky diode by Skyworks Solutions Inc. of Woburn, MA is used to design the voltage multiplier. During the negative cycle of the AC signal, a capacitor is charged through a diode and during the positive cycle of the AC signal, another capacitor is charged through another diode. During the next negative half cycle, the capacitor is discharged and allows a further capacitor to be charged through a further diode. During the next positive half cycle, yet another capacitor is charged through yet another diode. The output of the voltage multiplier is thus found to be the sum of the charges on another capacitor and yet another capacitor. For the low frequency applications of 1-10 Hz frequency range, the sizing of the capacitors can be chosen to be about 10 mF. A load capacitor of about 10 mF can be used to reduce the output ripples and a load resistance of 11 kΩ is used to emulate the total load of the system. The value of the load resistor is calculated based on the voltage and current requirements of the charge-amplifier, which requires a 3.3 V supply voltage and 300 µA current.

In some embodiments, as the output of the voltage multiplier varies with the varying harvested energy by the REWOD system, a voltage regulator may be needed to provide a constant voltage to the REWOD-based motion sensor read-out circuit. As an example, a TPS746-Q1 ultra low power low-dropout regulator (LDO) by Texas Instruments, Inc. of Dallas, TX with high power supply rejection ratio (PSRR) of 38 dB can be used to provide a constant voltage of 3.3 V. The commercial LDO can provide a constant 3.3 V output when the nominal input voltage is higher than 3.3 V. The LDO can have an input voltage range of 1.5 V to 6 V and an externally adjustable output voltage range of 0.55 V to 5.5 V. The LDO can be provided in various forms such as a WSON package with six pins. The input capacitor can be used to improve the transient response, input ripple, and PSRR. In some aspects, the input capacitor can have a value of 10 µF. If the input supply has a high impedance over a large frequency range, multiple capacitors can be used in parallel. An output capacitor can also be used for stability. In some aspects, the output capacity can have a value of 10 µF. The output of the LDO can be adjusted using a feedback resistive divider denoted by RFB and RPG. As an example, to achieve 3.3 V output, the chosen resistor values can be 10 kΩ and 4.3 kΩ for RFB and RPG, respectively.

During REWOD operation in some embodiments, charge is generated due to the electrode modulation. This charge may be converted to an AC voltage signal and amplified employing charge amplifier (CA)-based IEs. Any human physical activity producing charge can be transmitted wirelessly after the conversion of the charge to a voltage signal and amplification. The standard COTS-based charge amplifier may assess the generated charge from the REWOD. The CA converts the generated charge through an input capacitor and produces an output voltage ($V_{out}$) at the output node of the amplifier. The output voltage is directly proportional to the generated current of the REWOD. The output voltage can be obtained from the feedback capacitor, $C_f$ and the modulation frequency, f of the electrode displacement using the following equation:

$$V_{out} = I_{REWOD}/fC_f$$

where $I_{REWOD}$ is the generated current from the REWOD. The amplifier gain is set by the feedback resistor, $R_f$. A load capacitor is also connected to the output node in order to replicate the input capacitance of the next stage of the system that can either be a low-pass filter or an ADC. In some aspects, the input capacitance ($C_{in}$) may be chosen to be 12 nF to eliminate any DC components from the input AC signal. In some aspects, the gain resistor value (Rf) may be chosen to be 4.7 kΩ, to set the CA gain as 24 V/V.

In some embodiments, the rectifier circuit may be seven-stage voltage-doubler boosting rectifier circuit to achieve an output voltage of seven times the input voltage. The rectifier circuit may include SMS7630 Schottky diodes due to the low forward-bias voltage of the Schottky diode architecture. A single-stage voltage-doubler circuit diagram of the seven-stage rectifier circuit consists of two diodes and two capacitors. The architecture works as a full-wave rectifier where one diode operates during the positive half-cycle and the other diode operates during the negative half-cycle of the input AC signal. To reduce the ripple in the rectified output voltage of the rectifier, the capacitor values are chosen in such a way that the time constant is much larger than the period of the input signal in the following equations:

$$I_{rect}/2_\Pi \ll f$$

$$R_L C \gg T$$

where Lrect and Vrect are the output current and voltage of the rectifier, respectively, f is the frequency of the input voltage, $R_L$ is the load resistance, C is the output capacitance, and T is the time period of the input signal. The input and output capacitor values may be chosen to be 10 µF to produce a smoother DC signal at the output where the desired output current and voltage may be 4 mA and 700 mV, respectively. The current values may be chosen because of the current requirements of the DC-DC converter that is within 2-3 mA. As the DC-DC converter used may have a minimum threshold voltage of 700 mV, the minimum desired output voltage from the rectifier may be 700 mV. The seven-stage voltage boosting rectifier circuit may be designed for rectifying as low as 70 mVP-P input voltage. To design the rectifier, the Schottky diode with the minimum forward voltage of 135 mV for 1 mA forward current may be used.

A boost converter may be used as the voltage regulator. As an example, a TPS61220 by Texas Instruments, Inc. of Dallas, TX can be a highly efficient switching boost converter. To achieve high efficiency, a synchronous boost topology may be used as the power stage. For the power switching, two actively controlled MOSFETs having low on-resistance may be implemented. The input of the boost converter can receive varying DC voltages from the rectifier and provide a constant DC voltage at the output. The output DC voltage of the boost converter may depend on the external resistor divider varying on the application requirements. The input capacitor may help eliminate the fluctuations in the input voltage of the regulator to assist with the transient behavior. The output voltage may be regulated using a hysteretic current mode controller that may maintain the inductor's current constant at 200 mA. A feedback loop and an external reference voltage source may connect to a voltage error amplifier to drive the inductor current higher by increasing the voltage across the inductor. During steady-state operation, the inductor's current may charge the output capacitor and flow into the load.

If no bias voltage is applied to the REWOD energy harvester, the AC voltage generated within the REWOD due to the modulation of the electrolyte between the electrodes may be in the range of a few hundreds of millivolts for the frequency range of 1-3 Hz. The AC peak-to-peak voltage may increase linearly with increasing frequency between 1 to 3 Hz with an average slope of about 75 mV/Hz.

In some embodiments, as the current increases linearly with increasing frequency, so does the voltage, which can satisfy Ohm's law considering resistance remains constant. The AC voltage per unit area (VP-P/cm$^2$), may be determined based on the maximum electrode-electrolyte interfacial area during modulation. As an example, for a 50 µL electrolyte droplet and 2.5 mm displacement, the area may be calculated as 0.3 cm$^2$. Thus, the AC peak-to-peak voltage density (VP-P/cm$^2$) may be in the range of 0.32-0.8 VP-P/cm$^2$. The voltage generated across the REWOD electrodes as a result of a continuous change in capacitance and hence an alternating current along with the effective system resistance arising from the conductive layer, dielectric layers, and electrolyte.

In some embodiments, with the increasing electrode-electrolyte interfacial area, AC current increases resulting in an increase of AC voltage. The increase in AC voltage with increasing displacement may not be linear as with the increasing frequency. Rather, the increase may be almost parabolic. Although not wanting to be bound by theory, this increase in AC voltage may result as the electrode-electrolyte interfacial area is circular in geometry because the electrolyte can be sandwiched between the electrodes. As the circular contact area increases with increasing droplet deformation ($A=\pi r^2$), the AC voltage can increase almost parabolically. Hence, a parabolic relation of increasing AC voltage with respect to the increasing droplet deformation at a fixed oscillation frequency of 2 Hz can occur. As an example, from a 50 µL volume of electrolyte for the droplet deformation percentage between 24-34%, the AC voltage can be in the range of 71 mVP-P to 422 mVP-P. In terms of AC voltage per unit area (VP-P/cm$^2$), the voltage density may range from 0.39 VP-P/cm$^2$ to 0.97 VP-P/cm$^2$ for the given displacements. The range of AC voltage from the REWOD can be significant as completely arising within the electrode-electrolyte interface without any external voltage source.

The generated AC voltage signal from the REWOD can also be applied to the charge amplifier in order to produce an amplified output voltage while varying both the frequency and the droplet deformation. An amplified voltage over varying frequency band from 1 Hz to 3 Hz may be determined to be between 2.3 VP-P to 5.8 VP-P. The amplified output voltage proportionally can correspond with the measured AC voltage output from the REWOD in terms of linearity. Likewise, the amplified peak-to-peak voltage may be over the droplet deformation range of 24-34%. With the increasing displacement, the amplified voltage increased over the range, may not follow a linear trend, rather increased parabolically agreeing with the increasing trend of REWOD output voltage with increasing displacement. In order to pass all the current through the feedback path of the CA, the feedback capacitor (Cf) may be chosen to be 500 pF.

The AC signal harvested by the REWOD can be within the range of about 0.5 to about 8 Hz, or in the range of about 1 to 3 Hz, and the rectified voltage output may correspond. The minimum harvested AC signal may be about 94 mVP-P for the minimum 1 Hz frequency for which the output rectified voltage can be determined as 63 mV DC. The simulated and measured output DC voltage of the rectifier for different frequencies may have a step size of 0.25 Hz. The maximum measured output voltage can be 963 mV for the input AC voltage signal of 238 mVP-P at 3 Hz frequency. The diode SMS7630 may be created in simulation software by modifying the forward voltage and forward current according to the data sheet. The simulation may show higher voltage outputs compared to the measured voltages. This higher voltage output may be due to the simulation using the lossless ideal components to run the simulation. The rectified output voltage for the harvested AC voltage from the REWOD energy harvester may vary due to droplet deformations. The minimum harvested voltage at about 24% droplet deformation can be 71 mVp-p for which the measured rectified DC voltage may be 98 mV at 2 Hz frequency. A maximum DC voltage of 1.39 V may be measured at 34% droplet deformation.

The commercially available DC-DC converter model can be simulated using simulation software as well. The voltage range of the boost converter may be 0.7 to 5 V, which can require the minimum DC voltage output from the rectifier to be 0.7 V. The measured voltage output ($V_{out}$) of the boost converter may be 1 MΩ load resistor. The output voltage of the boost converter may be a constant 3 V when the $V_{rect}$ can be within 0.7 V to 3.3 V range. Above 3.3 V, $V_{out}$ increased slightly to 3.3 V. The minimum input voltage required for the DC-DC converter can be achieved when the rectifier input voltage is 200 mVP-P. When the input voltage is 200 mVP-P, the rectifier can be above 700 mV output for all three oscillation frequencies. The DC-DC converter can be able to generate 9 µW of DC power for an output load of 1 MΩ. The DC output power can scale up to 30 µW/cm$^2$ in terms of power density, which may be significant considering the volume of electrolyte used (50 µL) and 2.5 mm of electrode displacement.

Having described aspects of the REWOD sensor, a system using the REWOD sensor will now be discussed. Referring to FIG. 1, a person 1 or wearer 1 is schematically depicted with a motion sensor device 10. The person 1 can wear the motion sensor device 10 on a leg, an arm, or any suitable location where sufficient motion is created to generate energy, as discussed herein.

Figure 2:
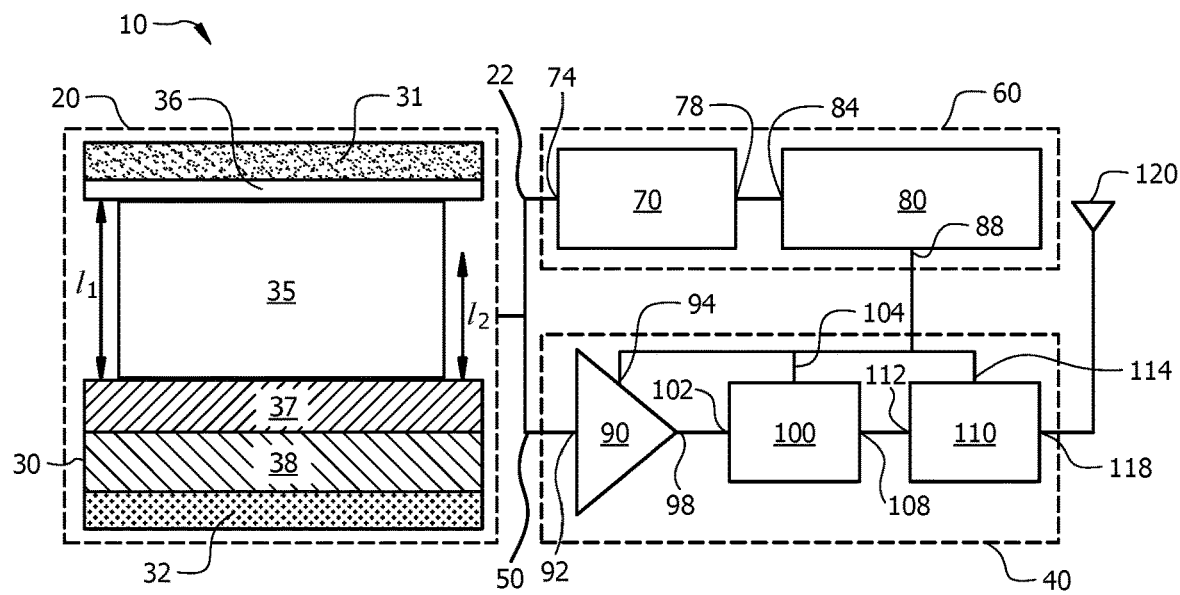
FIG. 2 is a schematic depiction of the motion sensor device according to an embodiment.

Regarding FIG. 2, an example of the motion sensor device 10 including a wireless motion sensor read-out circuit 40 is shown. Particularly, the motion sensor device 10 can include a REWOD generator 20, a motion sensor 30, the wireless motion sensor read-out circuit 40, and an energy harvesting system 60. The REWOD generator 20 may be configured to measure motion data and may include the motion sensor 30. In a further aspect, a motion sensor input 22 may be coupled to a REWOD-based motion sensor 30.

Figure 4:
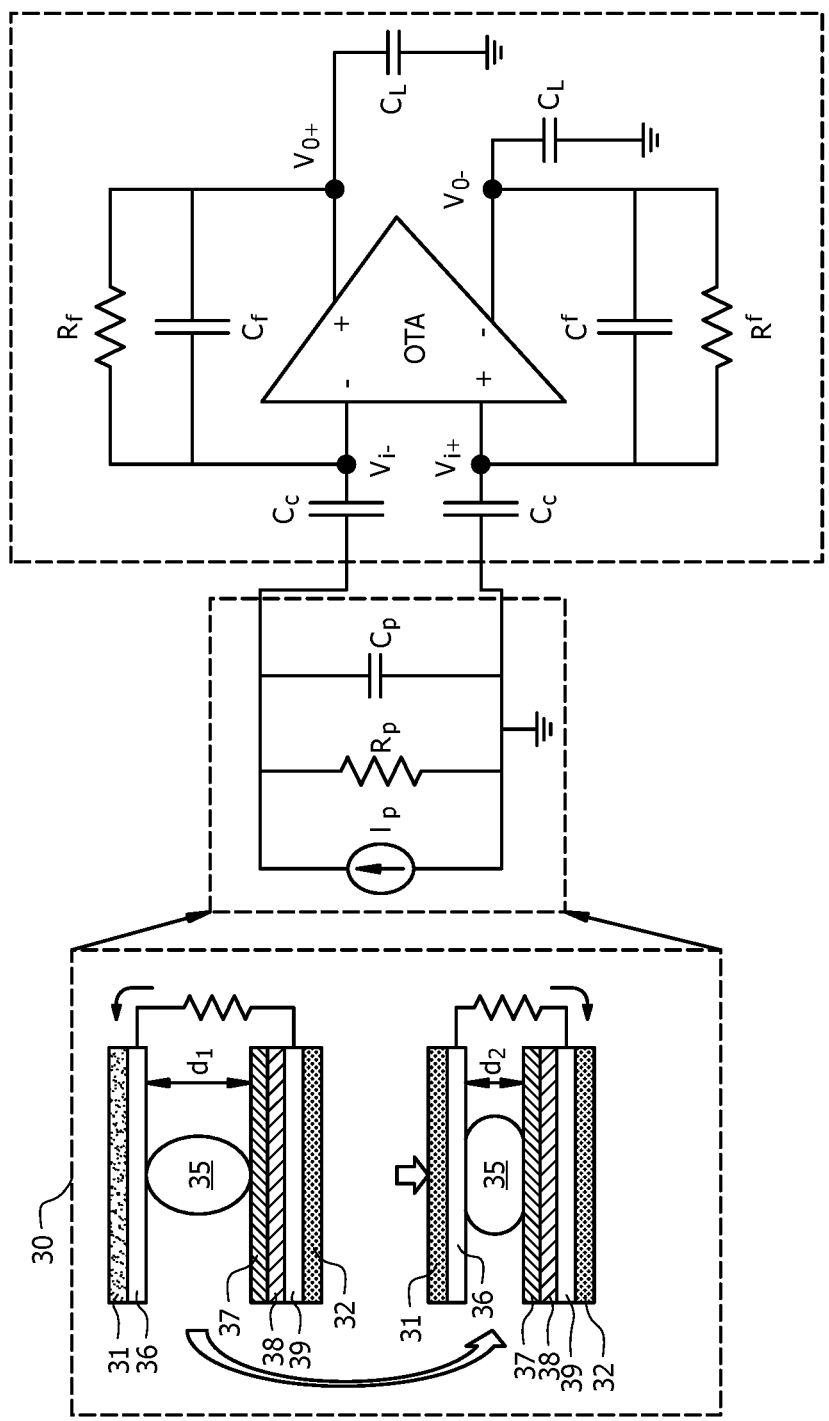
FIG. 4 is a schematic depiction of a reverse electrowetting energy harvester with amplification according to an embodiment.

The REWOD generator 20 may include the motion sensor 30, in turn, including a first conductive electrode 31, a second conductive electrode 32, an electrolyte 35, a metal layer 36 including, e.g., titanium, a hydrophobic layer 37 including, e.g., a fluoropolymer, and a dielectric layer 38 including, e.g., silicon dioxide. The REWOD generator 20 may comprise the conductive electrolyte 35 compressed and uncompressed between electrodes 31 and 32. Although not wanting to be bound by theory, the REWOD generator 20 generates AC by movement of the electrolyte 35, such as the conductive liquid droplet, squeezed between two electrodes 31 and 32. Generally, the electrolyte 35 changes height between $l_1$ to $l_2$ generating energy due to the wearer 1 moving the motion sensor device 10. In a further aspect, a power input 50 is coupled to a REWOD generator 20. The REWOD generator 20 may also comprise an on-chip amplifier. The on-chip amplifier may comprise an amplifier and a resistor capacitor (RC) network as shown in FIG. 4, and the energy generating action is described in further detail with respect to FIG. 4 below.

Figure 5:
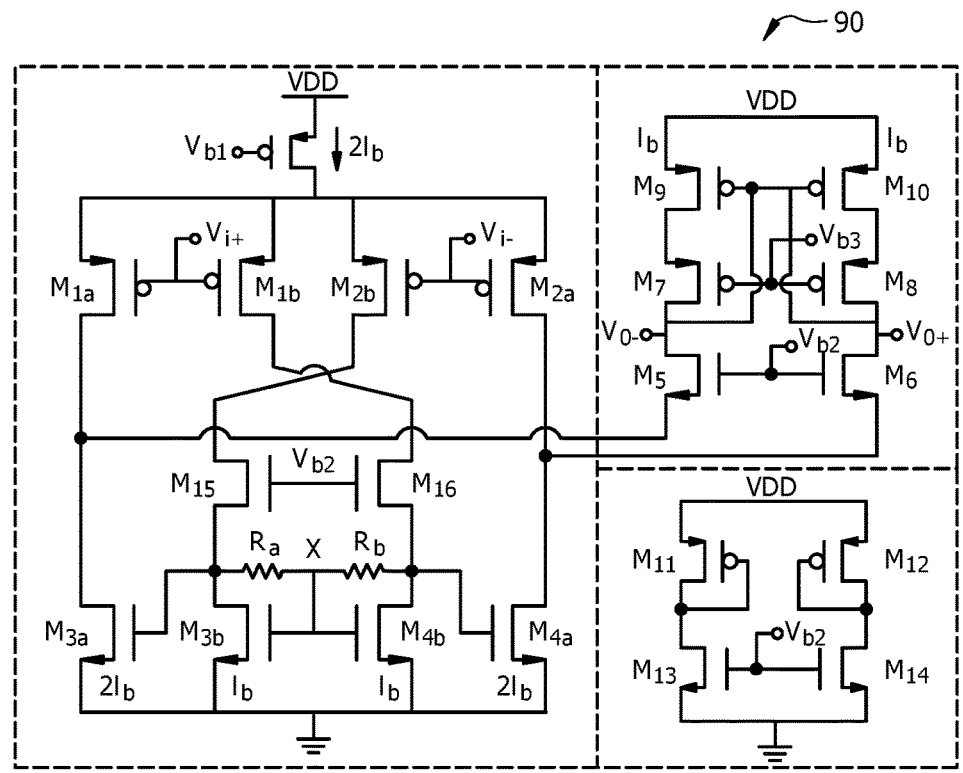
FIG. 5 is a schematic depiction of an amplifier according to an embodiment.

The wireless motion sensor read-out circuit 40 can be coupled to the REWOD generator 20 and the motion sensor 30. The wireless motion sensor read-out circuit 40 configured to transmit the motion data and operate on the AC from the REWOD generator 20. The wireless motion sensor read-out circuit 40 may include an amplifier 90, an analog to digital converter (ADC) 100, and a transmitter 110. Typically, the REWOD generator 20 powers the amplifier 90, analog to digital converter (ADC) 100, and transmitter 110. The power input 50 may be in communication with an amplifier input 92 coupled to the motion sensor input 22. The amplifier 90 may have an amplifier power port 94 coupled to a voltage regulator output 88, as described hereinafter, and an amplifier output 98. The amplifier 90 may further comprise pairs of p-channel enhancement mode metal-oxide semiconductor (pMOS) transistors. In some embodiments, motion data may be measured in analog, and wherein the wireless motion sensor read-out circuit 40 comprises the amplifier 90 configured to amplify the motion data. In a further aspect, the amplifier 90 may comprise a recycled folded-cascode operational transconductance amplifier (OTA), an input capacitor, and a capacitive feedback loop in a differential structure, as depicted in FIG. 4 and as described in further detail below. As a specific example, the amplifier 90 may be configured as depicted in FIG. 5 and as described in further detail below.

Figure 6:
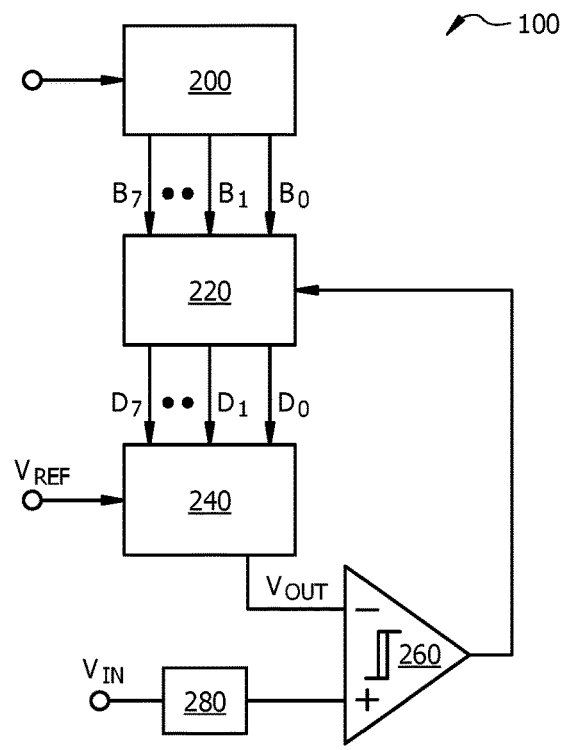
FIG. 6 is a schematic depiction of an analog-to-digital converter according to an embodiment.

The ADC 100 may include an ADC input 102 coupled to the amplifier output 98, an ADC power port 104 coupled to the voltage regulator output 88, and an ADC output 108. In a further aspect, the ADC 100 may comprise a shift register, a successive approximation register (SAR) logic circuit, a digital-to-analog (DAC) converter, a sample-and-hold circuit, and a comparator. For example, the ADC 100 may be configured as an eight-bit ADC. In some embodiments, the ADC 100 may be configured to convert the motion data into digital format. As a specific example, the ADC 100 may be configured as shown in FIG. 6 described in further detail hereinafter.

Figure 7:
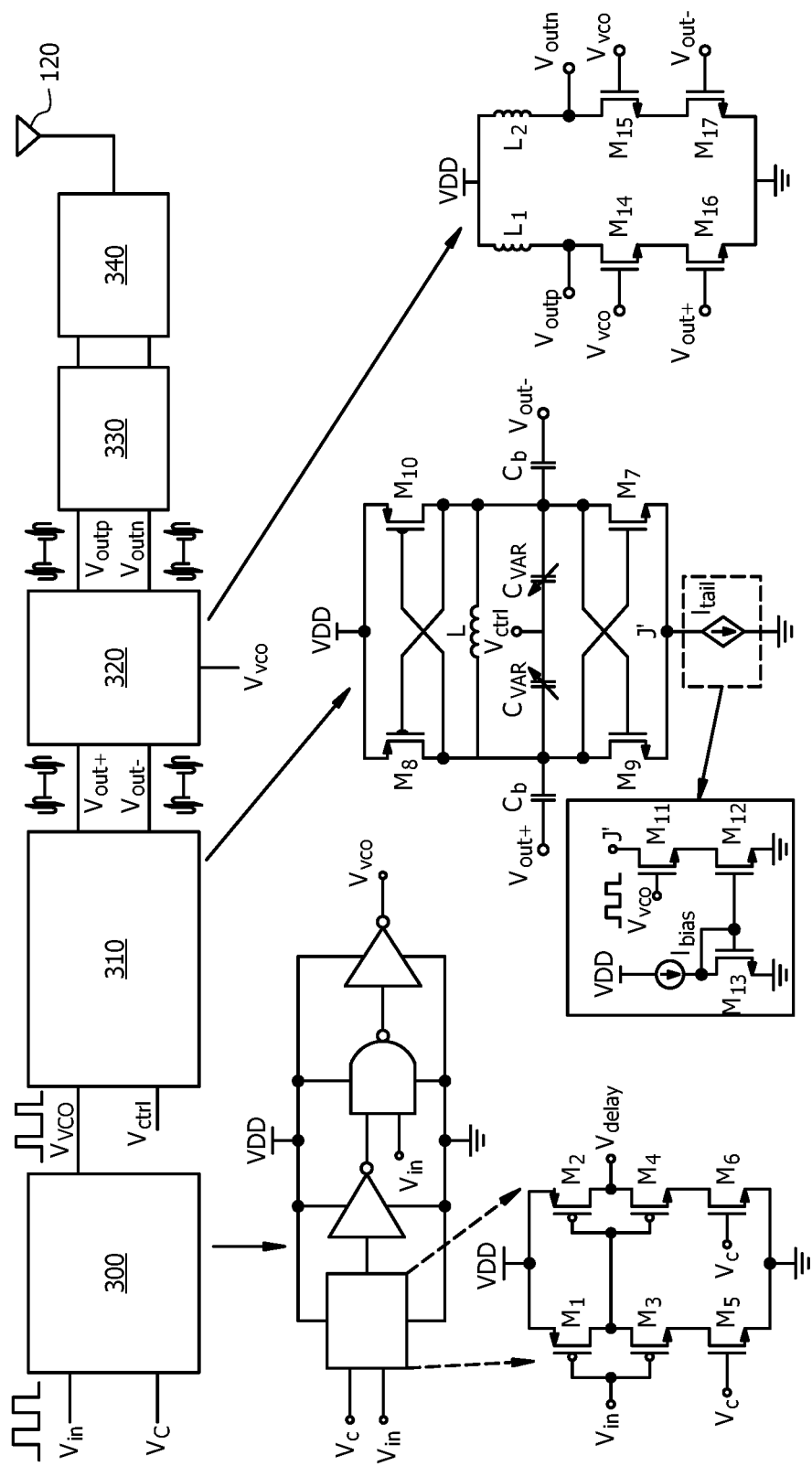
FIG. 7 is a schematic depiction of a transmitter according to an embodiment.

The transmitter 110 configured to transmit the motion data may include a transmitter input 112 coupled to the ADC output 108, a transmitter power port 114 coupled to the voltage regulator output 88, and a transmitter output 118. In a further aspect, the transmitter 110 may comprise an impulse-radio ultra-wideband (IR-UWB) transmitter circuit. Further, the transmitter 110 may comprise an impulse generator, a voltage-controlled oscillator, and a power amplifier. In an example, the impulse generator may be a current-starved inverter-based delay circuit. Further, the impulse generator may comprise a two-stage cascaded inverter circuit with pMOS transistors and n-channel enhancement mode metal-oxide semiconductor (nMOS) transistors. The impulse generator may further comprise an inverter, a not and (NAND) gate, and an inverter. As an example, the impulse generator may be a current-starved inverter-based delay circuit. In an example, the voltage-controlled oscillator is a complementary cross-coupled low phase-noise inductance capacitance voltage-controlled oscillator (LC-VCO) having two p-channel enhancement mode metal-oxide semiconductor (pMOS) and two n-channel enhancement mode metal-oxide semiconductor (nMOS) transistors. In an example, the power amplifier may comprise a choke inductor pair and two cascoded nMOS transistors in each branch. As a further example, the impulse generator may include a two-stage cascaded inverter circuit with pMOS transistors and nMOS transistors. As a specific example, the transmitter 110 may be configured as shown in FIG. 7 and as described in further detail below. The transmitter output 118 may be in communication with an antenna 120. The antenna 120 can communicate data to a receiving station for recording and analysis. The recording station may be a standard computer.

Figure 3:
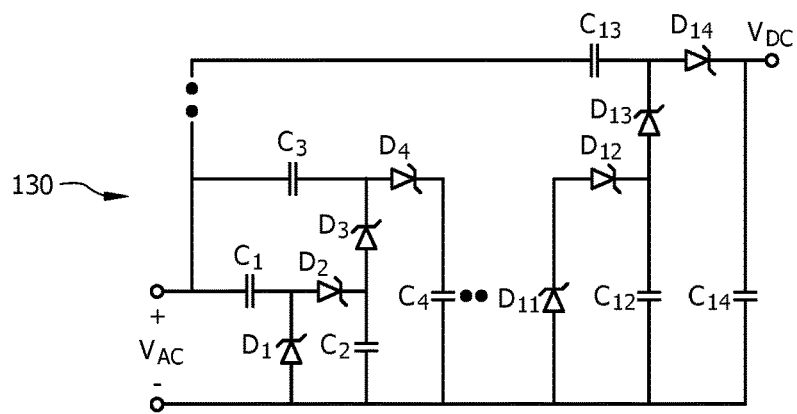
FIG. 3 is a schematic depiction of a seven-stage Schottky diode-based rectifier circuit according to an embodiment.

The energy harvesting system 60 may include a rectifier 70, which may be an AC to DC converter and a voltage regulator 80. In some embodiments, the wireless motion sensor read-out circuit 40 comprises at least one of a rectifier 70 configured to convert the AC into direct current (DC) and a voltage regulator 80 configured to maintain the DC at a substantially constant voltage. The rectifier 70 may include a rectifier input 74 coupled to the power input 50 and a rectifier output 78. In a further aspect, the rectifier 70 may comprise a seven-stage voltage doubler circuit. Further, the rectifier 70 may also comprise a full-wave rectifier. As a specific example, the rectifier 70 may comprise a network 130 of Schottky diodes and capacitors, as depicted in FIG. 3 and described hereinafter. The voltage regulator 80 may include a voltage regulator input 84 coupled to the rectifier output 78 and the voltage regulator output 88.

Referring to FIG. 3, the rectifier 70 may include a seven-stage Schottky diode based rectifier circuit 130. The rectifier circuit 130 may be a seven-stage voltage-doubler circuit using Schottky diodes due to the low forward-bias voltage of the Schottky diode architecture. A voltage doubler circuit consists of two diodes $D_1$, $D_2$ and two capacitors $C_1$ and $C_2$. The architecture may work as a full wave rectifier where $D_1$ operates during positive half cycle and $D_2$ operates during the negative half cycle of the input AC signal. The capacitor values are chosen to be 100 pF to produce a smoother DC signal at the output. The seven-stage voltage doubler circuit is designed so that it can rectify as low as 100 mV input voltage.

Referring to FIGS. 2 and 4, the REWOD energy harvesting system 60 may be the opposite to electrowetting operating at low-frequency range. In FIG. 4, a metal layer 39, including, e.g., titanium, is depicted and may be between the second conductive layer 32 and the dielectric layer 38. In its simplest form, the REWOD generator 20 can involve the conductive droplet 35 being repeatedly squeezed between the two electrodes 31 and 32. This results in a modulating electrical double layer (EDL) capacitance. The AC current generation due to the EDL capacitance change is shown in FIG. 4. The amount of current generated by the fabricated REWOD-transducer depends on the contact surface area between the conductive liquid (e.g. NaCl solution) 35 and the electrodes 31 and 32, which is correlated to the displacement. The bottom electrode 32 may be formed as a multi-layer structure with aluminum oxide ($Al_2O_3$) as the dielectric layer 38 and the fluoropolymer solution 37 as the hydrophobic material. One exemplary fluoropolymer solution is sold under the trade designation CYTOP® by Asahi Glass Company, Limited Corporation of Tokyo, Japan. The amorphous fluoropolymer 37 not only may makes the surface hydrophobic, but also acts as a secondary layer of dielectric in addition to $Al_2O_3$. As an initial approach to verify the phenomenon, the displacement between the top and bottom electrode is mechanically varied, thereby changing the contact surface area at certain input frequency. The fabricated device is modeled as an AC current source (Ip) with a parallel resistor (Rp) and a capacitor (Cp) as shown in FIG. 4. The average value of Rp and Cp is measured using the CHI600E potentiostat and found to be 7.44 MΩ and 94.6 nF, while Ip is in the range of 25-90 nAp-p.

As depicted in FIG. 4, the first state $d_1$ depicts an uncompressed conductive droplet 35. After movement by the wearer 1, the second state $d_2$ depicts a compressed conductive droplet 35. These repetitive uncompressed and compressed states can generate AC.

Referring to FIG. 5, an exemplary amplifier 90 is depicted. The change in motion-dependent surface charge density due to the mechanical vibration of the conductive liquid in the REWOD transducer can be converted to a proportional voltage signal by the charge amplifier 90. The charge amplifier 90 includes an OTA, an input capacitor ($C_C$) and the capacitive feedback loop ($R_f$ and $C_f$) in a fully differential structure as shown in FIG. 4. The amplifier 90 produces a voltage across $C_f$ which is proportional to the generated charge. The input impedance of the charge amplifier 90 is designed to be almost zero so that most of the current is passed through the amplifier 90. Keeping all these design constraints into consideration, the charge amplifier 90 is designed with a folded-cascode OTA with current recycling technique to have a high gain-bandwidth-product (GBW), low power consumption, and a high signal-to-noise ratio as shown in FIG. 5. As the gain depends on the product of the output impedance ($R_o$) and the transconductance ($G_m$), the input pair transistor of the conventional FC is split into two pairs: $M_{1a}$-$M_{1b}$ and $M_{2a}$-$M_{2b}$ in order to split the current from $2I_b$ to $I_b$. In this work, pMOS transistors are used as the input pair as this can reduce the flicker noise components compared to the nMOS transistors. The bottom transistors are also split into $M_{3a}$-$M_{3b}$ and $M_{4a}$-$M_{4b}$ to operate as the common-mode feedback current mirror along with the equal resistors $R_a$ and $R_b$. Because the node 'X' is floating, no current goes through the resistors. $G_m$ of the OTA can be expressed as follows:

$$G_m = 2(1 + g_{m,3a} R_a) g_{m,1a}$$

where $g_{m,3a}$ and $g_{m,1a}$ are the transconductances of the transistors $M_{3a}$ and $M_{1a}$, respectively. As the gain largely depends on $R_a$, its value is chosen as 25 kΩ to meet high open-loop gain specification. The current through the tail transistors ($M_{3a}/M_{3b}$) depends on the aspect ratio (W/L) of them. At the output stage, $M_5$-$M_6$ pair is sized as the transistors $M_{15}$-$M_{16}$ to have the same biasing. The bias voltages $V_{b2}$ and $V_{b3}$ are chosen to have the output current as $I_b$. Thus, the total bias current sums up to be $6I_b$. To reduce the power consumption of the OTA, $I_b$ is chosen to be 200 nA.

Referring to FIG. 6, an exemplary ADC 100 is depicted. The eight-bit ADC 100 is designed with a switched capacitor architecture based on charge redistribution logic. It includes a shift register, a SAR logic circuit, an eight-bit digital-to-analog (DAC) converter, a sample-and-hold circuit, and a comparator. The ADC 100 is designed to have a low-power consumption and a sampling frequency of 1 ksamples/s, as the motion sensing signals would lie in a low-frequency bandwidth (typically 0.1 to 10 Hz). The ADC 100 may include an eight-bit shift register 200 communicating directly with a SAR 220, in turn directly communicating with a digital-to-analog converter (DAC) 240. The DAC 240 and a sample and hold (S/H) circuit 280 can communicate with a comparator output 260 providing feedback to the SAR 220.

Referring to FIG. 7, an embodiment of the transmitter 110 is depicted including a circuit. The IR-UWB transmitter circuit consists of an impulse generator (IG), a voltage controlled oscillator (VCO) 310 and a power amplifier (PA) 320. The can transmit digitized sensed signal with 100 kbps data rate. The transmitter 110 includes an impulse generator 300, the voltage controlled oscillator 310, the power amplifier 320, a matching network 330 and a balun electrical device 340.

The impulse generator 300 uses a current-starved inverter based delay circuit where the output pulse Vdelay of the delay circuit is controlled using an external control voltage Vc. The circuit is made of two-stage cascaded inverter circuit using pMOS and nMOS transistors. The delay circuit is followed by an inverter, a NAND gate and an inverter to generate the impulse signal which is used for duty-cycling the VCO 310 and the PA 320. The impulse generator 300 can communicate with the voltage controlled oscillator 310.

The voltage controlled oscillator 310 is a complementary cross-coupled LC-VCO having two pMOS and two nMOS transistors. The W/L ratio of the transistor M7-M9 and M8-M10 are set in such a way to operate in the strong inversion region to ensure high Gm. The LC tank of the VCO 310 includes an inductor, L of 2.7 nH and a varactor pair, $C_{VAR}$ which achieves a capacitance in the range of 4.5-17 pF for the control voltage, $V_{ctrl}$ of 100 mV to 1.8 V range. The varactor pair is used to achieve the oscillation frequency f0 in the range 3.5-5 GHz with the total capacitance, $C = C_{VAR} C_b C_{gd,M8} C_{gd,M9}$. At the output of the VCO 310, a 300 fF DC blocking capacitor, $C_b$ is also used to block the DC components of the generated RF signal. The tail current source of the VCO 310 is actually a current mirror formed by transistor $M_{12}$ and $M_{13}$. To duty-cycle the VCO 310, the pulse signal generated by the impulse generator is used at the gate of the transistor $M_{11}$ that turns on and off the tail current source of the VCO 310. The VCO 310 can communicate with the power amplifier 320.

The power amplifier 320 may be a differential class E power amplifier that includes a choke inductor pair $L_1$-$L_2$ and two cascoded nMOS transistors in each branch. Optimum sizes of the transistors may be chosen to have small on-resistance and small parasitic capacitance. The PA 320 is duty-cycled using the pulse signal $V_{VCO}$ at the gate of the transistors $M_{14}$ and $M_{15}$. The differential output signal of the VCO 310 is provided to the gate of $M_{16}$ and $M_{17}$. To feed the differential output of the PA 320 to the single-ended antenna 120, the matching network 330 and the balun electrical device 340 is used after the PA 320.

In some embodiments, the AC signal harvested from the REWOD generator for human motion activities such as walking and running is of very low frequency (1-3 Hz) and amplitude (95-240 mV). The low-frequency signal can be rectified and the rectified DC voltage ($V_{rect}$) can be boosted to a certain constant voltage using pump circuits or converters according to the system requirement without using any external sources. Some embodiments herein can rectify and voltage boost with circuitry designed for the signal generated by the REWOD energy harvester. Desirably, the entire circuit does not require any external supply voltage to make the transducer and the circuit completely self-powered. The REWOD generator generates current as the person walks and/or runs, which is provided as an input to the rectifier and DC-DC voltage booster circuit. REWOD has been demonstrated to effectively generate electrical current proportional to the displacement at the low-frequency range of 1-10 Hz, which is the frequency range for various physical activities of a human being such as running, jogging, walking, etc. Output that captured in the REWOD generator is given to the AC-DC boost rectifier as an input. Some embodiments include the following architecture of the rectifier and DC-DC voltage converter circuits.

In some embodiments the rectifier is a transistor-level implementation using NMOS transistors. With the help of cross-coupling capacitors the design circuit can convert AC to DC voltage. The output from the REWOD generator is provided as an input to the rectifier. The AC voltage signal generated by the REWOD is around 100-250 mV with a frequency range of 1-10 Hz.

A bridge rectifier or any other diode-based rectifiers cannot be suitable for this signal as the output from the REWOD generator is as low as 100 mV and the diode will only conduct at 700 mV (0.67 V in exact) voltage. So, using MOSFET's with cross-coupling capacitors is preferred for the design. All NMOS transistors where positive and negative peaks of the input AC signal are rectified by the circuit. The circuit is a three-stage boost rectifier where each stage of the circuit is for better smoothing and boosting the signal.

When the output from the REWOD generator is given to the rectifier, transistors are connected according to diode connected transistor. During positive cycle, one CMOS transistor is ON and the other CMOS transistor is OFF so the positive cycle is rectified. Similarly during the negative cycle, one CMOS transistor is ON and the other CMOS transistor is OFF so the negative cycle is rectified, in this way both positive and negative cycles are rectified and cascaded to the next stage. During every stage, the DC output is boosted. If a 180 nm CMOS process using the ideal capacitance with the time constant being much larger than the input signal period so the capacitance is taken as 1 nF and NMOS transistors of length (L) is 180 nm and width (W) is 220 nm with a load resistance of 10 MΩ according to the current requirement, the circuit is designed as such. More stages can also be added, but by increasing more components the power consumption with-in the circuit increases. So, three-stages may be preferred for better output. Thereafter, that rectified voltage from the rectifier (Vrect) is provided to the five-stage DC-DC voltage booster.

In some embodiments, a DC-DC booster is utilized, can be a voltage doubler circuit or a charge pump. So, adding multiple stages of this circuit can obtain the desired output DC voltage. The circuit can reduce the power consumption by the transistors so, taking low L and W values can result in high efficiency during the output. In this design five-stages of cross-coupled switched capacitor are cascaded and implemented using CTS (NMOS charge transfer switches) technique designed by using four MOSFETs and two transfer capacitors in each stage. Each stage can include two latched CMOS pairs. The transfer capacitors of each stage are alternately charged to the voltage of the previous stage and then boosted by $V_{rect}$ to charge the next stage at a higher voltage. During the first half cycle when φ1 is high (φ2(=phi 1) is low) transistors are ON, and other transistors are OFF, transfer capacitor is charged to $V_{rect}$ through the other CMOS transistor, while transfer capacitor is boosted to $V_{rect}+V\varphi1$ through one CMOS transistor. During the second half cycle, transistors are turned ON, and other transistors are turned OFF, transfer capacitor is charged to $V_{rect}$, while transfer capacitor is boosted to $V\varphi1+V_{rect}$. Once NMOS has enough gate-source voltage then PMOS (the CMOS starts charging and similarly for the CMOS transistors, thereby the output transfers to the next stage. The clock frequency can be 1 k Hz.

Some embodiments provide a self-powered on-chip motion sensor that acquires the motion detecting signal and transmits the signal wirelessly. The on-chip rectifier provides the DC supply voltages to the recording circuitry: amplifier, ADC, as well as to the transmitter. The full system can be implemented on a flexible substrate to remotely monitor motion activities of the body.

Some embodiments provide the integration of an AC-DC rectifier and a DC-DC boost converter circuit designed in 180 nm CMOS process for ultra-low frequency (<10 Hz) energy harvesting applications. The rectifier is a very low voltage CMOS rectifier circuit that rectifies the low-frequency signal of 100-250 mV amplitude and 1-10 Hz frequency into DC voltage. The energy is harvested from the REWOD (reverse electrowetting-on-dielectric) generator, which is a reverse electrowetting technique that converts mechanical vibrations to electrical energy. A REWOD-based self-powered motion (such as walking, running, jogging, etc.) tracking sensors can be worn, thus harvesting energy from regular activities. To this end, the circuits are designed in such a way that the output from the REWOD is rectified and regulated using a DC-DC converter which is a five-stage cross-coupled switching circuit. A voltage range of 1.1 V-2.1 V, i.e., 850-1200% voltage conversion efficiency (VCE) and 30% power conversion efficiency (PCE) for low input signal in the range 100-250 mV in the low frequency range. This performance verifies the integration of the rectifier and DC-DC boost converter which makes it highly suitable for various motion-based energy harvesting applications.

Some embodiments provide a 180 nm CMOS technology standards a three-stage boost rectifier and a five-stage DC-DC boost converter. A very-low AC voltage of 100 mV can be converted and boosted into 1.2 V DC voltage and 250 mV of AC voltage input can be converted into 2.1 V DC voltage, improving efficiency and optimization. Hereby, the self-generated current from the REWOD generator is effectively converted and boosted into appropriate DC voltage applicable for various harvesting circuits.

In some embodiments, various energy harvesting technologies to generate electrical energy from ambient energy sources can be used. Many energy harvesters currently available are limited by their power output and energy densities. With the miniaturization of wearable and implantable electronics, the size of the harvesters is preferably miniaturized accordingly in order to increase the energy density of the harvesters. Additionally, many of the energy harvesters also suffer from limited operational parameters such as resonance frequency and variable input signals. In this work, low frequency motion energy harvesting based on reverse electrowetting-on-dielectric (REWOD) is examined using perforated high surface area electrodes with 38 μm pore diameters. Total available surface area per planar area is 8.36 $cm^2$ showing a significant surface area enhancement from planar to porous electrodes and proportional increase in AC voltage density. In REWOD energy harvesting, high surface area electrodes significantly increase the capacitance and hence the power density. An AC peak-to-peak voltage generation from the electrode in the range from 1.57-3.32 V for the given frequency range of 1-5 Hz with 0.5 Hz step is demonstrated. In addition, the unconditioned power generated from the harvester is converted to a DC power using a commercial off-the-shelf Schottky diode-based voltage multiplier and low dropout regulator (LDO) such that the sensors that use this technology can be fully self-powered.

The produced charge is then converted to a proportional voltage by using a commercial charge amplifier to record the features of the motion activities. A transceiver radio is also used to transmit the digitized data from the amplifier and the built-in analog-to-digital converter (ADC) in the microcontroller. The energy harvester can act as a self-powered motion sensor for different physical activities for wearable and wireless healthcare devices.

In some embodiments, REWOD-based high surface area energy harvesting can be implemented using a perforated high surface area porous silicon wafer electrode with 51,784 pores, each with a diameter of 38 µm within a circular area of 3.14 cm$^2$ and without application of the bias voltage. Generated AC voltage due to the continuous charging and discharging of the electrodes can be measured with respect to varying frequency. The AC voltage generation from the REWOD in the oscillation frequency range of 1-5 Hz with 0.5 Hz step size can be in the range of about 1.58-3.32 V. This range of frequency aligns very well with various human motion activities such that the REWOD energy harvested from human motion could potentially power WIEs without requiring an external energy source. The DC output voltage from the multiplier for the range of AC voltage from REWOD can be measured in the range of 3.6-4 V. A single unit device may be comprised of the REWOD energy harvester and the components for power conditioning and amplification can be integrated together and worn on an arm, an ankle, or a knee, etc. for motion sensing to detect whether a person is at rest, walking, or running as part of human health monitoring in real time.

In some embodiments, a reverse electrowetting-on-dielectric (REWOD) energy harvester integrated with rectifier, boost converter, and charge amplifier that is, without bias voltage, capable of powering wearable sensors for monitoring human health in real-time. REWOD has been demonstrated to effectively generate electrical current at a low frequency range (<3 Hz), which is the frequency range for various human activities such as walking, running, etc. However, the current generated from the REWOD without external bias source is insufficient to power such motion sensors. In some embodiments, to eventually implement a fully self-powered motion sensor, a novel bias-free REWOD AC generation and can then rectify, boost, and amplify the signal using commercial components. In an example, the unconditioned REWOD output of 95-240 mV AC can be generated using a 50 µL droplet of 0.5M NaCl electrolyte and 2.5 mm of electrode displacement from an oscillation frequency range of 1-3 Hz. A seven-stage rectifier using Schottky diodes having a forward voltage drop of 135-240 mV and a forward current of 1 mA can convert the generated AC signal to DC voltage. A potential difference of about 3 V DC is measured at the boost converter output, demonstrating the system could function as a self-powered motion sensor. Additionally, a linear relationship of output DC voltage with respect to frequency and displacement demonstrates the potential of this REWOD energy harvester to function as a self-powered wearable motion sensor.

In some embodiments, REWOD based mechanical motion energy harvesting can be implemented without requiring any external bias voltage. The AC voltage across the electrodes due to AC current generation with continuous charging and discharging of the electrodes can be measured with respect to varying frequency and electrode displacements. As an example, the AC voltage from the REWOD with respect to frequency (13 Hz) for 2.5 mm displacement can be in the range of about 95-240 mV for a 50 µL droplet of electrolyte. Similarly, the AC voltage from the REWOD with respect to droplet deformation from 24% to 34% due to varying electrode displacements at 2 Hz oscillation frequency can be in the range of 71-422 mV. This range of frequency and displacement align very well with various human motion activities, but the voltage is too low for practical applications. Therefore, the REWOD AC voltage can be converted to a constant DC power source using a multistage rectifier, and a DC-DC boost converter. Likewise, the rectified DC voltage of 0.7 V can provide a constant 3 V of output voltage through the boost DC-DC converter signifying that the REWOD energy harvester with integrated charge amplifier and boost converters can be used as a self-powered motion sensor. In some embodiments, a single unit device that comprises the REWOD energy harvester and the components for power conditioning and amplification can be integrated together and worn on an arm, an ankle, or a knee, etc. for motion sensing to detect whether a person is at rest, walking, or running as part of human health monitoring in real time.

Additional advantages may be apparent to one of skill in the art viewing this disclosure.

EXAMPLES

The embodiments having been generally described, the following examples, as described in the Appendix, are given as particular embodiments of the disclosure and to demonstrate the practice and advantages thereof. It is understood that the examples are given by way of illustration and are not intended to limit the specification or the claims in any manner.

Example 1

The power conversion efficiency (PCE) of the rectifier is for the input voltage range of 100 mV to 1.4 V. The maximum PCE is simulated to be 62% with the load resistance RL as 1 M Ω. The harvested DC power from the motion sensor is measured after the single-stage rectification. As the REWOD transducer is modulated from 1.5 mm to 4 mm displacement, the generated DC power increases over the motion frequency. The closed-loop gain of the charge amplifier is 53.7 dB. As the gain depends on the ratio of the input and feedback capacitances, the values are chosen as 1 nF and 2 pF, respectively. The feedback resistor is designed to maintain the lower cut-off frequency at 1 Hz. Because the motion sensor is designed to detect low-frequency signal, the higher cut-off frequency is kept as 150 Hz. The total bias current is 1.2 µA in order to reduce the power consumption to 2.35 µW. The input-referred noise is 3.8 µVrms integrated over 1 to 200 Hz frequency band. After the amplification, the ADC converts the analog voltage signal to 8 digital bits at 1 ksamples/s with a total power consumption of 277 µW, and effective number of bits of 6.8.

Example 2

An impulse signal of 1.8 V is generated with a pulse width of 5 ns for 100 kbps data rate when the control voltage Vc is 600 mV and consumes 800 pW power for 1.8 V supply voltage. Varying the control voltage Vc from 100 mV to 600 mV, the pulse width of the impulse signal can be varied as high as 10 µs to 720 ps respectively which enables a reconfigurable bandwidth of 500 MHz-1.39 GHz. Varying the control voltage Vctrl from 800 mV to 1.4 V, the operating frequency of the VCO can vary from 3.5-4.5 GHz. The pulse width of the output signal is recorded as 5 ns with a maximum voltage of 1.7 Vpp. The gain of the PA is simulated to be 6 dB for the frequency range of 3.5-4.5 GHz. From the output of the PA, the power spectral density (PSD) of the transmitted signal is also simulated. The center frequency is at 4 GHz where the peak amplitude is −43.6 dBm/MHz with a −10 dB bandwidth of 700 MHz. The average power consumption of the transmitter is 105 pW for 1.8 V supply voltage and the energy efficiency of the transmitter is simulated to be 8.5 pJ/pulse at 100 kbps data rate. The on-chip amplifier, ADC, and transmitter consume a total of ~280 µW.

Example 3

The simulation results of the rectifier and the DC-DC converter circuit can include the voltage out versus the voltage in of the rectifier. The output voltage boosts the input voltage linearly at frequency range of 1-10 Hz. The minimum voltage to conduct this circuit is 80 mV and output voltage at 80 mV is 190 mV. The voltage conversion efficiency is versus input voltage at different frequencies from 1-10 Hz. The plot lines are voltage conversion efficiency for 2 Hz, 4 Hz, 6 Hz, 8 Hz, 10 Hz frequencies respectively with an input voltage range of 100 mV-250 mV AC. At this range the output voltage range is 250 mV-1.1V DC.

Example 4

Where the output voltage is at different frequencies, the input voltage can be used to calculate the voltage conversion efficiency. The results are obtained from the simulation. When input voltage increases, the voltage conversion efficiency increases, and at higher input voltage of 250 mV at 10 Hz, it can be observed higher voltage conversion efficiency of nearly 420% and the VCE range is 250-420%.

Examples 5

The power conversion efficiency is versus power in of the rectifier. At 25 0 mV at 10 Hz frequency, the PCE is 15%. The figure is plotted between different input voltages at different frequencies. To achieve more power efficiency, adjusting W, L and number of fingers of MOSFET can be done.

Example 6

When the 100 mV of AC the output, the DC voltage is 1.18 V. Increasing the input voltage linearly increases the output DC voltage. The output voltage range at 100-250 mV input AC voltage is 1.2-2.1 V DC. The voltage conversion efficiency versus input AC voltage (100250 mV) from the REWOD may be analyzed. At 250 mV at 10 Hz of the frequency, the average output DC voltage is 2.1 V, which is high enough to be used as a supply voltage for the load of some devices, such as sensors and transducers. The VCE range is between 840-1220%.

Example 7

The power conversion efficiency at different frequencies may be compared, as well as between power conversion efficiency of power out and input power in. For the corresponding input according to voltage in of the range of 100-250 mV, the PCE range is 15-30%. From the observation both VCE and PCE, a 100 mV input with 2 Hz frequency both VCE and PCE efficiencies are 1200% and 30% respectively.

Example 8

A very low resistance (0.001-0.005 Ω-cm), 100 mm diameter, and 380 µm thick double side polished silicon wafer from University Wafers Inc. of Boca Raton, FL (hereinafter "University Wafers") is used to fabricate the porous electrode with 38 µm diameter uniform pores within a circular area of 3.14 cm² (1 cm radius). A high-resolution chrome mask is created from an AutoCAD of San Rafael, CA generated DXF file for the given pore pattern. A positive photoresist sold under the trade designation KL6008 from Kemlab Inc. of Woburn, MA is spin coated on the wafer at 300 rpm for 5 seconds (spread cycle) and 600 rpm for 45 seconds (spin cycle). This process provides a sufficient photoresist thickness of about 10-12 µm as required for safe deep reactive ion etching (DRIE) later in the fabrication process. The photoresist is cured for 150 seconds at 105° C. on a hot plate. The cured wafer is then exposed under UV light for 45 seconds at 210 mJ/cm² of exposure broadband. Subsequently, the UV-exposed wafer is immediately developed using tetramethylammonium hydroxide, 0.26N (0.26N tetramethylammonium hydroxide (TMAH)) developer for about 2 minutes, rinsed with deionized water, and dried with nitrogen air. The pore patterns and the photoresist thickness on the developed wafer are verified using a profiler sold under the trade designation Alpha-Step D-300 Stylus Profiler of KLA Corporation of Milpitas, CA (hereinafter "KLA"). The patterned wafer is etched to create through pores using deep reactive ion etching (DRIE) sold under the trade designation Oxford100 ICP of Oxford Instruments PLC of Abingdon, United Kingdom in the Nanofab facility at the University of Utah. The etched porous wafer is subjected to plasma CVD sold under the trade designation Oxford Plasmalab 80 of Oxford Instruments PLC of Abingdon, United Kingdom and deposited with $SiO_2$ dielectric. The anisotropic plasma DRIE is performed in the presence of sulfur hexafluoride ($SF_6$) at a flow rate of 80 sccm and octafluorocyclobutane ($C_4F_8$) at a flow rate of 90 sccm under a vacuum pressure of 7.5 µtorr. Once etched, the wafers are thoroughly cleaned before carbon vapor deposition (CVD) deposition of $SiO_2$. A wafer may be patterned with photoresist using photolithography. A wafer with 38 µm diameter pores after DRIE is subsequently deposited with $SiO_2$. Because the entire wafer is coated with $SiO_2$ during CVD and CYTOP dip coating, a small portion of the wafer is treated with hydrofluoric acid (HF) to remove the $SiO_2$ and a CYTOP® fluoropolymer coating for an electrical connection to a wire lead.

A custom-built measurement set-up for the high surface area REWOD energy harvesting is constructed consisting of a subwoofer generating pulsating pressure through a vertical displacement of a piston inside an attached syringe. The syringe is attached to a 3D printed stage over the subwoofer dust cap and only the piston is allowed to move in a vertical direction. The subwoofer is controlled by a signal generating application sold under the trade designation Audio Function Generator PRO from MTI Instruments of Albany, NY (hereinafter "Audio"). This application works almost the same way as an actual function generator except exciting the subwoofer in vertical mechanical displacement to a desired amplitude. The shaker system consists of an 8-inch 800-W subwoofer from Pyle USA of New York City, NY (hereinafter "Pyle"), a 400 W amplifier sold under the trade designation CX250 from Boss Corporation a subsidiary of Roland Corporation of Hamamatsu, Japan (hereinafter "Boss"), and a 12-V power source sold under the trade designation ATX Raptor of Apevia Corporation of Industry, CA (Apevia) attached to a power adapter cord. Similar custom-made systems have been reported in prior energy harvesting research. This set-up can provide a simple, inexpensive method for generating low-frequency and relatively high amplitude oscillations. A custom wood enclosure provided a location to mount the subwoofer and also contained the amplifier and power source.

The master volume feature in the mobile application corresponds to the amplitude of the vertical displacement of the syringe piston and hence the magnitude of the pressure generated. The pressure magnitude is higher for a higher frequency oscillation at a fixed master volume. Pressure can be precisely controlled as desired by adjusting the amplitude for any given frequency in the application. Pulsating pressure generated in the form of sinusoidal peak-to-peak pressure for a frequency range of 1-5 Hz with 1 Hz step size are measured using a pressure sensor (PASCO PS-320) and are approximately within the range of 1.5-16 kPa. This range of pressure is well within the range of Laplace capillary pressure required for the insertion and retraction of electrolyte in and out of pores for all pore sizes in this work. The Laplace capillary pressure, as shown in the following equation, is the pressure that is required for liquid to penetrate into the micropores.

$$P = 2\gamma \cos\theta / r$$

where $\gamma$ is the surface tension, $\theta$ is the contact angle, and r is the pore radius. The pressure that the subwoofer system is capable of generating straddles the Laplace capillary pressure. Once the pulsating pressure generated by the subwoofer system reaches the capillary pressure at a given frequency, the liquid electrolyte is inserted in and retracted out of the pores. This liquid movement results in a periodically changing electrode-electrolyte interfacial area, resulting in a periodic change in charge, which produces an AC current.

Before the actual measurements of AC voltage began, several trial AC voltage measurements are performed by applying pulsating pressure in small increments starting with a lower limit (about 1.5 kPa) to observe any increase in the magnitude of the AC voltage. In order to ensure that an optimum peak-to-peak pressure for all pore sizes is identified such that there is neither excess pressure to cause electrolyte leakage from the porous electrode to the bottom chamber nor is there insufficient pressure inhibiting the electrolyte to cover the entire pore walls. Applied pressure from the pulsating pressure device is gradually increased to realize a proportional increase in the magnitude of the AC voltage until the AC signals disappeared from the oscilloscope indicating electrolyte leakage beneath the porous electrode. The pressure immediately before the lamented signal is adopted as the optimum peak-to-peak pressure. Theoretical capillary pressure is given by the Laplace equation shown in the equation above, where $\gamma = 0.072$ N/m and $\theta = 110°$, and is calculated for the given pore size. The Laplace pressure is determined to be 2.6 kPa and the corresponding experimental peak pressure is 2.8 kPa showing good agreement on pulsating pressure. The error percentage of 7.2, which is the difference between the theoretical and experimental peak pressure, may be attributed to a possible air pressure leakage during the experiment.

The REWOD energy harvesting unit may consist of hollow upper and bottom chambers. The upper chamber is an aluminum housing and acts both as a counter electrode as well as an airtight compartment to prevent pressure leakage during experiment. The bottom housing is a 3D printed poly lactic acid (PLA) fixture to support the electrode (the porous silicon wafer). The electrode is sealed on either side with silicone O-rings with the same circular area to that of the porous section of the electrodes (3.14 $cm^2$). Once the REWOD energy harvesting unit is secured, deionized water, which is used as an electrolyte in this work, is injected into the top housing to completely cover the porous area of the electrode. Afterwards, the AC voltage measurement is performed.

Examples 9

The working mechanism of the high surface area REWOD energy harvester is the generation of AC voltage through periodically changing electrode-electrolyte interfacial area from an externally applied mechanical force, the pulsating pressure. AC voltages for the electrode are measured for a frequency range of 1-5 Hz with 0.5 Hz step size using an oscilloscope sold under the trade designation InfiniiVision DSOX3014A from Keysight Technologies, Inc. from Santa Rosa, CA (hereinafter "Keysight") while applying 2.8 kPa of experimentally determined peak pulsating pressure. The AC peak-to-peak voltage ranges from 1.57-3.32 V for the given frequency range. The peak-to-peak voltage for the 38 μm diameter pore electrode has a frequency range of 1-5 Hz with 0.5 Hz step. The AC voltage increases approximately linearly with frequency. Coefficient of determination ($R^2$ value) and slope from the plot are determined to be 0.99 and 0.47 respectively showing a linear regression of AC voltage with increasing frequency. A representative plot of measured AC voltage is versus time over a 3-second time period for the 38 μm pore size electrode at 3.0 Hz. The DC offset (difference between the maximum positive and negative peak) of 0.14 V and an amplitude of 2.36 V are measured from the data in the plot. The magnitude of the voltage is significant realizing that no bias voltage has been applied in the experiment.

Examples 10

The generated charge in the REWOD electrodes is converted into the proportional voltage in the charge amplifier. The signal is digitized in the built-in microcontroller with a reference voltage of 1.65 V. The digitized signal is then transmitted through the transceiver and ceramic antenna. The transmission data rate of 250 ksamples/s is used. After the remote receiver receives the digitized motion signal, it is reconstructed back into analog signal in LabVIEW GUI system-design platform and development environment (digital-to-analog converter) from National Instruments of Austin, TX A representative signal of the motion data at 3 Hz oscillation frequency for the first 3 seconds can show the reconstructed signal after the motion data is sent wirelessly to the remote receiver.

In parallel with the charge amplifier, the AC energy harvested by the REWOD system is rectified using the voltage multiplier circuit. The input voltage peak-to-peak denotes the harvested AC voltage for the frequency range of 1-5 Hz with a step size of 0.5 Hz. For the lowest harvested AC voltage of 1.52 V at 1 Hz, the voltage multiplier is able to provide an output DC voltage of 3.6 V and for the highest input voltage of 3.3 V at 5 Hz frequency, the output DC voltage of the voltage multiplier is found to be 3.99 V. The maximum power conversion efficiency (PCE) is calculated to be 21% for 1 Hz frequency. The rectified DC voltage of the respective frequency is then used as the input of the LDO circuit, which is designed to provide a constant 3.3 V as output. The output voltage, $V_{LDO}$, shows a constant voltage of 3.3 V when the LDO input voltage is above 3.3 V. For 1 Hz frequency, the system achieves the lowest harvested energy resulting in the lowest rectified voltage of 3.6 V, which can still provide 3.3 V at the output of the LDO circuit. The total DC power provided by the system is approximately 1 mW for 3.3 V output voltage and 327 µA output current.

Example 11

Two dissimilar electrodes are fabricated using (single-side polished) highly doped P-type silicon wafers with a diameter of 50.5 mm and a thickness of 0.38 mm (University Wafers). Both wafers are first coated with about a 100-nm-thick titanium adhesion layer. Before the deposition of dielectric material over the titanium layer, a small portion of the wafer is covered with a polyimide film with silicon adhesive tape sold under the trade designation KAPTON® of DuPont de Nemours, Inc. of Wilmington, DE, to block the dielectric insulation and later is removed to enable current conduction. A 100-nm-thick dielectric material ($Al_2O_3$) is deposited on one of the wafers. Both the titanium and dielectric materials are deposited using the dual e-beam evaporator sold under the trade designation NEE-400 by Nanomaster Inc. of Austin, TX After each deposition, thicknesses are verified using the profiler sold under the trade designation Alpha-Step D-300Stylus Profiler by KLA. After a successful deposition of the desired thickness of the dielectric, an additional layer of hydrophobic fluoropolymer, CYTOP®, is deposited. The fluoropolymer CYTOP® (CTL-809M), and its solvent (CT-Solv. 180), are both purchased from AGC Chemicals Company of Exton, PA, are mixed in a volumetric ratio of 1:3. The solution is spin-coated on the wafer over the dielectric layer using a spin coater sold under the trade designation WS-650MZ of Laurell Technologies Corporation of North Wales, PA Spin coating is performed at 600 rpm for 5 seconds (spread cycle) and then at 3,000 rpm for 50 seconds (spin cycle). The sample is dried at room temperature for 15 minutes, pre-baked for 30 minutes at 80° C., and finally baked again for 60 minutes at 185° C. to ensure complete evaporation of the solvent. A complete dielectric electrode sample has a layered electrode structure. A SEM image of the cross-section is obtained using a field-emission scanning electron microscopy sold under the trade designation JSM-7001F from Joel USA, Inc. of Peabody, MA to confirm the thickness and uniformity of different deposited layers.

Approximately 20 mL of 0.5M aqueous solution is prepared using sodium chloride from Sigma Aldrich Inc., a subsidiary of Merck KGaA of Darmstadt, Germany, and deionized water is used as an electrolyte. Many REWOD experiments in the past have used electrolytes that are either expensive such as Galinstan (gallium-indium-tin) or toxic such as mercury. Sodium chloride solution is chosen as a charged form of electrolyte which is not only a convenient form of electrolyte, but is also cost effective. However, in practical REWOD application, use of salt solution as an electrolyte may not be feasible.

Example 12

The experimental setup for the AC signal (VP-P) generation and measurement consists of an XYZ positioner stage with a long and lightweight acrylic beam attached to it. The beam is used to hold the top electrode stationary. The XYZ positioner is used to set a 4 mm gap between the top and bottom electrodes before the modulation starts. Input oscillations are applied using a custom-built subwoofer system that can be controlled with a signal generating app from Audio. The shaker system consists of an 8-inch 800-W subwoofer (Pyle), a 400 W amplifier (Boss), and a 12-V power source (ApeviaC) attached to a power adapter cord. This method of producing low-frequency and high-amplitude oscillations has been used in prior published work. A custom wood enclosure provides a location to mount the subwoofer and contains the amplifier and power source. A 3D-printed sample-holding stage is placed over the subwoofer dust cap to provide a flat surface to hold the bottom REWOD substrate. During the electrolyte modulation between the electrodes, generated AC voltage at various subwoofer oscillation frequencies are measured using an oscilloscope (Keysight). The displacement amplitude for each subwoofer frequency is determined by measuring the vertical distance between the electrodes during the modulation using a slow-motion cell phone camera and a ruler. For each frequency step, the amplitude is adjusted in the function generator to replicate the desired displacement.

Example 13

AC voltage is generated by how much the droplet is squeezed with varying electrode displacements in the vertical direction at 2 Hz frequency and is measured using the same set-up as that of varying frequency. The bottom electrode substrate has a constant oscillation of +/− 1.25 mm. The initial gap between the top and bottom electrodes range from 3.65 mm to 5.25 mm with a step size of 0.2 mm and is precisely controlled using the micrometer scale on the XYZ stage. The resulting droplet deformation percentage in the y-direction, compared to initial gap distance, is 24% to 34%.

Having described various systems and methods herein, certain embodiments can include, but are not limited to:

In a first aspect, a wireless motion sensor read-out circuit comprises: a power input; a motion sensor input; a rectifier comprising a rectifier input and a rectifier output, the rectifier input coupled to the power input; a voltage regulator comprising a voltage regulator input and a voltage regulator output, the voltage regulator input coupled to the rectifier output; an amplifier comprising an amplifier input, an amplifier power port, and an amplifier output, the amplifier input coupled to the motion sensor input and the amplifier power port coupled to the voltage regulator output; an analog to digital converter (ADC) comprising an ADC input, an ADC power port, and an ADC output, the ADC input coupled to the amplifier output and the ADC power port coupled to the voltage regulator output; and a transmitter comprising a transmitter input, a transmitter power port, and an antenna, the transmitter input coupled to the ADC output and the transmitter power port coupled to the voltage regulator output.

A second aspect can include the wireless motion sensor read-out circuit of the first aspect, wherein the rectifier comprises a seven-stage voltage doubler circuit.

A third aspect can include the wireless motion sensor read-out circuit of the first or second aspect, wherein the rectifier further comprises a full wave rectifier.

A fourth aspect can include the wireless motion sensor read-out circuit of any one of the first to third aspects, wherein the rectifier further comprises Schottky diodes and capacitors.

A fifth aspect can include the wireless motion sensor read-out circuit of any one of the first to fourth aspects, wherein the amplifier comprises a folded cascode operational transconductance amplifier (OTA), an input capacitor, and a capacitive feedback loop in a differential structure.

A sixth aspect can include the wireless motion sensor read-out circuit of any one of the first to fifth aspects, wherein the amplifier further comprises pairs of p-channel enhancement mode metal-oxide semiconductor (pMOS) transistors.

A seventh aspect can include the wireless motion sensor read-out circuit of any one of the first to sixth aspects, wherein the ADC comprises a shift register, a successive approximation register (SAR) logic circuit, a digital-to-analog (DAC) converter, a sample-and-hold circuit, and a comparator.

An eight aspect can include the wireless motion sensor read-out circuit of any one of the first to seventh aspects, wherein the ADC is an eight-bit ADC.

A ninth aspect can include the wireless motion sensor read-out circuit of any one of the first to eighth aspects, wherein the transmitter is an impulse-radio ultrawideband (IR-UWB) transmitter circuit.

A tenth aspect can include the wireless motion sensor read-out circuit of any one of the first to ninth aspects, wherein the transmitter comprises an impulse generator, a voltage-controlled oscillator, and a power amplifier.

An eleventh aspect can include the wireless motion sensor read-out circuit of any one of the first to tenth aspects, wherein the impulse generator is a current-starved inverter-based delay circuit.

A twelfth aspect can include the wireless motion sensor read-out circuit of any one of the first to eleventh aspects, wherein the impulse generator comprises a two-stage cascaded inverter circuit with p-channel enhancement mode metal-oxide semiconductor (pMOS) transistors and n-channel enhancement mode metal-oxide semiconductor (nMOS) transistors.

A thirteenth aspect can include the wireless motion sensor read-out circuit of any one of the first to twelfth aspects, wherein the impulse generator further comprises an inverter, a not and (NAND) gate, and an inverter.

A fourteenth aspect can include the wireless motion sensor read-out circuit of any one of the first to thirteenth aspects, wherein the voltage-controlled oscillator is a complementary cross-coupled low phase-noise inductance capacitance voltage-controlled oscillator (LC-VCO) having two p-channel enhancement mode metal-oxide semiconductor (pMOS) and two n-channel enhancement mode metal-oxide semiconductor (nMOS) transistors.

A fifteenth aspect can include the wireless motion sensor read-out circuit of any one of the first to fourteenth aspects, wherein the power amplifier comprises a choke inductor pair and two cascoded n-channel enhancement mode metal-oxide semiconductor (nMOS) transistors in each branch.

A sixteenth aspect can include the wireless motion sensor read-out circuit of any one of the first to fifteenth aspects, wherein the power input is coupled to a reverse-electrowetting on dielectric (REWOD) generator.

A seventeenth aspect can include the wireless motion sensor read-out circuit of any one of the first to sixteenth aspects, wherein the motion sensor input is coupled to a reverse-electrowetting on dielectric (REWOD)-based motion sensor.

In an eighteenth aspect, a motion sensor device comprises: a reverse electrowetting-on-dielectric (REWOD) generator configured to generate alternating current (AC) based on motion; a motion sensor configured to measure motion data; and a wireless motion sensor read-out circuit coupled to the REWOD generator and the motion sensor, the wireless motion sensor read-out circuit configured to transmit the motion data and operate on the AC from the REWOD generator.

A nineteenth aspect can include the motion sensor device of the eighteenth aspect, wherein the REWOD generator generates AC by movement of a conductive liquid droplet squeezed between two electrode substrates.

A twentieth aspect can include the motion sensor device of the eighteenth or nineteenth aspect, wherein the wireless motion sensor read-out circuit comprises a rectifier configured to convert the AC into direct current (DC).

A twenty first aspect can include the motion sensor device of any one of the eighteenth to twentieth aspects, wherein the wireless motion sensor read-out circuit further comprises a voltage regulator configured to maintain the DC at a substantially constant voltage.

A twenty second aspect can include the motion sensor device of any one of the eighteenth to twenty first aspects, wherein the motion data is measured in analog, and wherein the wireless motion sensor read-out circuit further comprises an amplifier configured to amplify the motion data.

A twenty third aspect can include the motion sensor device of any one of the eighteenth to twenty second aspects, wherein the wireless motion sensor read-out circuit further comprises an analog to digital converter (ADC) configured to convert the motion data into digital format.

A twenty fourth aspect can include the motion sensor device of any one of the eighteenth to twenty third aspects, wherein the wireless motion sensor read-out circuit further comprises a transmitter configured to transmit the motion data.

A twenty fifth aspect can include the motion sensor device of any one of the eighteenth to twenty fourth aspects, wherein the amplifier, the ADC, and the transmitter are powered by the AC generated by the REWOD generator.

For purposes of the disclosure herein, the term "comprising" includes "consisting" or "consisting essentially of" Further, for purposes of the disclosure herein, the term "including" includes "comprising," "consisting," or "consisting essentially of."

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

While embodiments of the invention have been shown and described, modifications thereof can be made by one skilled in the art without departing from the spirit and teachings of the invention. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$, and an upper limit, $R_U$, is disclosed, any number falling within the range is specifically disclosed. In particular, the following numbers within the range are specifically disclosed: $R=R_L+k*(R_U-R_L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

What is claimed is:

1. A wireless motion sensor read-out circuit comprising:
a power input;
a motion sensor input;
a rectifier comprising a rectifier input and a rectifier output, the rectifier input coupled to the power input;
a voltage regulator comprising a voltage regulator input and a voltage regulator output, the voltage regulator input coupled to the rectifier output;
an amplifier comprising an amplifier input, an amplifier power port, and an amplifier output, the amplifier input coupled to the motion sensor input and the amplifier power port coupled to the voltage regulator output;
an analog to digital converter (ADC) comprising an ADC input, an ADC power port, and an ADC output, the ADC input coupled to the amplifier output and the ADC power port coupled to the voltage regulator output; and
a transmitter comprising a transmitter input, a transmitter power port, and an antenna, the transmitter input coupled to the ADC output and the transmitter power port coupled to the voltage regulator output.

2. The wireless motion sensor read-out circuit of claim 1, wherein the rectifier comprises a seven-stage voltage doubler circuit.

3. The wireless motion sensor read-out circuit of claim 2, wherein the rectifier further comprises a full wave rectifier.

4. The wireless motion sensor read-out circuit of claim 3, wherein the rectifier further comprises Schottky diodes and capacitors.

5. The wireless motion sensor read-out circuit of claim 1, wherein the amplifier comprises a folded cascode operational transconductance amplifier (OTA), an input capacitor, and a capacitive feedback loop in a differential structure.

6. The wireless motion sensor read-out circuit of claim 5, wherein the amplifier further comprises pairs of p-channel enhancement mode metal-oxide semiconductor (pMOS) transistors.

7. The wireless motion sensor read-out circuit of claim 1, wherein the ADC comprises a shift register, a successive approximation register (SAR) logic circuit, a digital-to-analog (DAC) converter, a sample-and-hold circuit, and a comparator.

8. The wireless motion sensor read-out circuit of claim 7, wherein the ADC is an eight-bit ADC.

9. The wireless motion sensor read-out circuit of claim 1, wherein the transmitter is an impulse-radio ultrawideband (IR-UWB) transmitter circuit.

10. The wireless motion sensor read-out circuit of claim 9, wherein the transmitter comprises an impulse generator, a voltage-controlled oscillator, and a power amplifier.

11. The wireless motion sensor read-out circuit of claim 10, wherein the impulse generator is a current-starved inverter-based delay circuit.

12. The wireless motion sensor read-out circuit of claim 11, wherein the impulse generator comprises a two-stage cascaded inverter circuit with p-channel enhancement mode metal-oxide semiconductor (pMOS) transistors and n-channel enhancement mode metal-oxide semiconductor (nMOS) transistors.

13. The wireless motion sensor read-out circuit of claim 12, wherein the impulse generator further comprises an inverter, a not and (NAND) gate, and an inverter.

14. The wireless motion sensor read-out circuit of claim 10, wherein the voltage-controlled oscillator is a complementary cross-coupled low phase-noise inductance capacitance voltage-controlled oscillator (LC-V CO) having two p-channel enhancement mode metal-oxide semiconductor (pMOS) and two n-channel enhancement mode metal-oxide semiconductor (nMOS) transistors.

15. The wireless motion sensor read-out circuit of claim 10, wherein the power amplifier comprises a choke inductor pair and two cascoded n-channel enhancement mode metal-oxide semiconductor (nMOS) transistors in each branch.

16. The wireless motion sensor read-out circuit of claim 1, wherein the power input is coupled to a reverse-electrowetting on dielectric (REWOD) generator.

17. The wireless motion sensor read-out circuit of claim 1, wherein the motion sensor input is coupled to a reverse-electrowetting on dielectric (REWOD)-based motion sensor.

* * * * *